United States Patent
Tanabe et al.

(10) Patent No.: US 8,109,909 B2
(45) Date of Patent: Feb. 7, 2012

(54) MEDICAL INSTRUMENT

(75) Inventors: Hidenori Tanabe, Nakakoma-gun (JP);
Ryoji Kobayashi, Nakakoma-gun (JP);
Takato Murashita, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/935,540

(22) PCT Filed: Mar. 26, 2009

(86) PCT No.: PCT/JP2009/056191
§ 371 (c)(1),
(2), (4) Date: Nov. 10, 2010

(87) PCT Pub. No.: WO2009/123026
PCT Pub. Date: Oct. 8, 2009

(65) Prior Publication Data
US 2011/0054404 A1    Mar. 3, 2011

(30) Foreign Application Priority Data

Mar. 31, 2008 (JP) ................................. 2008-093547

(51) Int. Cl.
*A61M 5/178* (2006.01)
(52) U.S. Cl. .............................................. 604/167.01
(58) Field of Classification Search ............ 604/164.01, 604/164.02, 165.01, 165.02, 165.03, 167.01
See application file for complete search history.

(56) References Cited

U.S. PATENT DOCUMENTS

| | | | | |
|---|---|---|---|---|
| 4,180,068 A | * | 12/1979 | Jacobsen et al. | 604/44 |
| 4,931,049 A | * | 6/1990 | Klimas | 604/165.01 |
| 5,250,038 A | * | 10/1993 | Melker et al. | 604/264 |
| 6,004,294 A | | 12/1999 | Brimhall et al. | |
| 6,749,588 B1 | | 6/2004 | Howell et al. | |
| 2004/0092889 A1 | | 5/2004 | Ferguson et al. | |
| 2007/0282417 A1 | * | 12/2007 | Houston et al. | 623/1.1 |

FOREIGN PATENT DOCUMENTS

| | | |
|---|---|---|
| JP | 2002-511319 A | 4/2002 |
| JP | 2006-505378 A | 2/2006 |
| JP | 2006-055674 A | 3/2006 |
| WO | WO 2007/052656 A1 | 5/2007 |
| WO | WO 2007/122959 A1 | 11/2007 |

OTHER PUBLICATIONS

International Search Report (PCT/ISA/210) issued on May 19, 2009, by Japanese Patent Office as the International Searching Authority for International Application No. PCT/JP2009/056191.
Written Opinion (PCT/ISA/237) issued on May 19, 2009, by Japanese Patent Office as the International Searching Authority for International Application No. PCT/JP2009/056191.

* cited by examiner

*Primary Examiner* — Nicholas Lucchesi
*Assistant Examiner* — Aarti B Berdichevsky
(74) *Attorney, Agent, or Firm* — Buchanan, Ingersoll & Rooney PC

(57) ABSTRACT

An indwelling needle assembly has a hollow outer needle fixed to an outer needle hub, an inner needle in the outer needle and fixed to an inner needle hub, and a protector. A step section of the outer needle hub serves as a speed reducer that reduces the speed, in the direction of the flow path axis of a main pipe, of a liquid portion flowing in the flow path, the portion flowing along that portion of the inner surface of the main pipe located on that side of the main pipe on which a branch flow path is located. The step section has an opening in the inner surface of the main pipe located at a position corresponding to a front end opening of the branch flow path. The step section forms a space between the opening and the front end opening of the branch flow path.

10 Claims, 22 Drawing Sheets

MEDICAL INSTRUMENT

TECHNICAL FIELD

The present invention relates to a medical instrument.

BACKGROUND ART

When an infusion is performed on a patient, or in other similar situations, an indwelling needle connected to an infusion line is made to puncture a blood vessel of the patient and the needle is left indwelling in the patient's blood vessel during the operation.

Such an indwelling needle (indwelling needle assembly) is composed of a hollow outer needle, an outer needle hub secured to a proximal end (base end) of the outer needle, an inner needle that is inserted in the outer needle and which has a sharp needle tip at a distal end (tip) thereof, and an inner needle hub secured to a proximal end of the inner needle. The outer needle hub is provided with a main pipe having a flow path that communicates with a lumen of the outer needle, and a side pipe having a branch flow path branching from the flow path of the main pipe. The infusion line is connected to the side pipe. (See, for example, Patent Document 1.)

When the indwelling needle punctures the patient's blood vessel, the puncturing operation is performed in a condition where the inner needle is inserted into the outer needle, and the needle tip of the inner needle protrudes from the distal end of the outer needle.

Once the needle tip of the inner needle has reached the inside of the blood vessel, blood flows into the inner needle through a distal portion thereof. The blood, in its course, flows through a hole formed in a side portion of the inner needle and into a flow path between the outer needle and the inner needle. The blood flows through the flow path, and then flows into the inside of the transparent outer needle hub. More specifically, the blood flows into the flow path of the main pipe, and further flows through the main pipe into the branch flow path of the side pipe (flashback). Consequently, it can be confirmed (visually checked) that the inner needle has captured (securely reached the inside of) the blood vessel.

After flashback is confirmed, the outer needle is advanced using the inner needle as a guide, and the outer needle is inserted into (allowed to puncture) the blood vessel.

Next, while grasping the outer needle hub, the inner needle is pulled out of the outer needle. Then, an infusion agent is administered through the infusion line, the side pipe and the main pipe of the outer needle hub, and the outer needle, which are in connection with one another.

However, the aforementioned conventional indwelling needle assembly has the following drawback. During a process in which, after the needle tip of the inner needle has reached the inside of the blood vessel, the blood passes through the flow path between the outer needle and the inner needle and flows into the flow path of the main pipe of the outer needle hub, and then through the main pipe into the branch flow path of the side pipe, bubbles (air) tend to remain in a part of the flow path of the main pipe that is located in the vicinity of the side pipe.

Patent Document 1: U.S. Pat. No. 6,749,588

DISCLOSURE OF THE INVENTION

An object of the present invention is to provide a medical instrument, with which it is possible to prevent a problem in that bubbles are left in a part of a flow path of a main pipe that is located in the vicinity of a side pipe, when a liquid is allowed to flow in the medical instrument.

In order to attain the above object, the present invention provides, a medical instrument including a main pipe and a side pipe having a branch flow path branching from a flow path of the main pipe, wherein speed reducing means is provided for reducing a speed, in an axial direction of the main pipe, of a portion of liquid that flows in the flow path of the main pipe, the portion being a portion that flows along a part of an inner surface of the main pipe, which is located on a side of the main pipe on which the branch flow path is located.

According to the present invention, as noted above, it is possible to prevent a problem in which bubbles (air) are left in a portion of the flow path of the main pipe near the side pipe when the liquid is allowed to flow therethrough. More specifically, when the liquid flows from the flow path of the main pipe into the branch flow path of the side pipe, the speed, in an axial direction of the main pipe, of a portion of the liquid that flows in the flow path of the main pipe is reduced. The portion of the liquid is a portion that flows along a part of the inner surface of the main pipe, which is located on a side of the main pipe on which the branch flow path is located. Therefore, when the speed is reduced, the bubbles are sent out into the branch flow path by the liquid portion that flows along the other parts, and the bubbles are discharged to the exterior through the branch flow path.

In addition, in the medical instrument of the present invention, preferably, the speed reducing means has an opening formed in the inner surface of the main pipe, and the flow path of the main pipe and the branch flow path of the side pipe communicate with each other by way of the opening.

This makes it possible to securely prevent a problem in which bubbles remain in the flow path of the main pipe in the vicinity of the side pipe when the liquid is allowed to flow therethrough.

Further, in the medical instrument of the present invention, preferably, the opening has a profile including a rectilinear portion substantially perpendicular to the axis of the main pipe, and the rectilinear portion is located on an upstream side with respect to a flow of liquid from a side of the main pipe toward a side of the side pipe.

This makes it possible to reduce the speed of the liquid that flows toward an edge confronting the rectilinear portion of the opening. More specifically, the liquid is temporarily (momentarily) stopped at the edge due to surface tension. This makes it possible to obviate the problem in which bubbles (air) remain in the flow path of the main pipe when the liquid is allowed to flow therethrough.

In addition, in the medical instrument of the present invention, preferably, the opening is polygonal in shape.

This makes it possible to reduce the speed of the liquid that flows toward an edge confronting the rectilinear portion of the opening. More specifically, the liquid is temporarily (momentarily) stopped at the edge due to surface tension. This makes it possible to prevent the problem in which bubbles (air) remain in the flow path of the main pipe when the liquid is allowed to flow therethrough.

Further, in the medical instrument of the present invention, preferably, the speed reducing means comprises a step section, which forms a space between the opening and a tip, on the main pipe side, of the branch flow path.

This makes it possible to reduce the speed of the liquid flowing toward an edge confronting the rectilinear portion of the opening. More specifically, the liquid is temporarily (momentarily) stopped at the edge due to surface tension. This makes it possible to obviate the problem in which bubbles (air) remain in the flow path of the main pipe when the liquid is allowed to flow therethrough.

In addition, in the medical instrument of the present invention, preferably, the step section has, at an edge thereof confronting the opening, an edge with an angle of not more than 90°.

This ensures that the speed of the liquid can be reduced more assuredly.

Further, in the medical instrument of the present invention, preferably, the speed reducing means comprises a projection, which is formed to project on the inner surface of the main pipe.

This ensures that the liquid flowing toward the projection can be dammed up temporarily (momentarily) (i.e., it is possible to reduce the speed, in the axial direction, of the liquid that flows along the part of an inner surface of the main pipe, which is located on the side on which the branch flow path is located). Consequently, it is possible to prevent the problem in which bubbles (air) remain in the flow path of the main pipe.

In addition, in the medical instrument of the present invention, preferably, the projection is located on an upstream side, with respect to the flow of liquid from a side of the main pipe toward a side of the side pipe, relative to a tip opening of the branch flow path connected to the flow path of the main pipe, and which is located in the vicinity of the tip opening.

This ensures that the liquid flowing toward the projection can be dammed up temporarily (momentarily) (i.e., it is possible to reduce the speed, in the axial direction, of the liquid that flows along the part of an inner surface of the main pipe, which is located on the side on which the branch flow path is located). Consequently, it is possible to prevent the problem in which bubbles (air) remain in the flow path of the main pipe.

Further, in the medical instrument of the present invention, preferably, the projection has a shape so as to cover substantially an entire part of the tip opening, as viewed in the axial direction of the main pipe.

This ensures that the liquid flowing toward the projection can be dammed up temporarily (momentarily) (i.e., it is possible to reduce the speed, in the axial direction, of the liquid that flows along the part of an inner surface of the main pipe, which is located on the side on which the branch flow path is located). Consequently, it is possible to prevent the problem in which bubbles (air) remain in the flow path of the main pipe.

In addition, in the medical instrument of the present invention, preferably, sealing means for sealing the flow path of the main pipe is provided at a part of the flow path of the main pipe that is located on the downstream side, with respect to the flow of liquid from a side of the main pipe toward a side of the side pipe, relative to the branch flow path.

This ensures that leakage of liquid is prevented from occurring, and than an aseptic condition inside the outer needle hub and the infusion line is secured.

Further, the medical instrument of the present invention, preferably, comprises an indwelling needle provided on a tip side of the main pipe.

This ensures that a puncturing operation can be performed on a living body surface, and that the punctured state can be maintained.

In addition, in the medical instrument of the present invention, preferably, the indwelling needle comprises a hollow outer needle in which an inner needle is inserted, and an outer needle hub, which is fixed to a base end part of the outer needle, incorporates therein the main pipe, the side pipe and the speed reducing means.

This enables the medical instrument of the present invention to be applied to an indwelling needle assembly.

BEST MODE FOR CARRYING OUT THE INVENTION

Next, a medical instrument according to the present invention will be described in detail below, based on preferred embodiments shown in the accompanying drawings.

Incidentally, while the present invention is applicable to various medical instruments, which include a main pipe and a side pipe having a branch flow path branching from a flow path of the main pipe, in the following embodiments, a case shall be described representatively in which the medical instrument of the present invention is applied to an indwelling needle assembly.

First Embodiment

Figure 1:
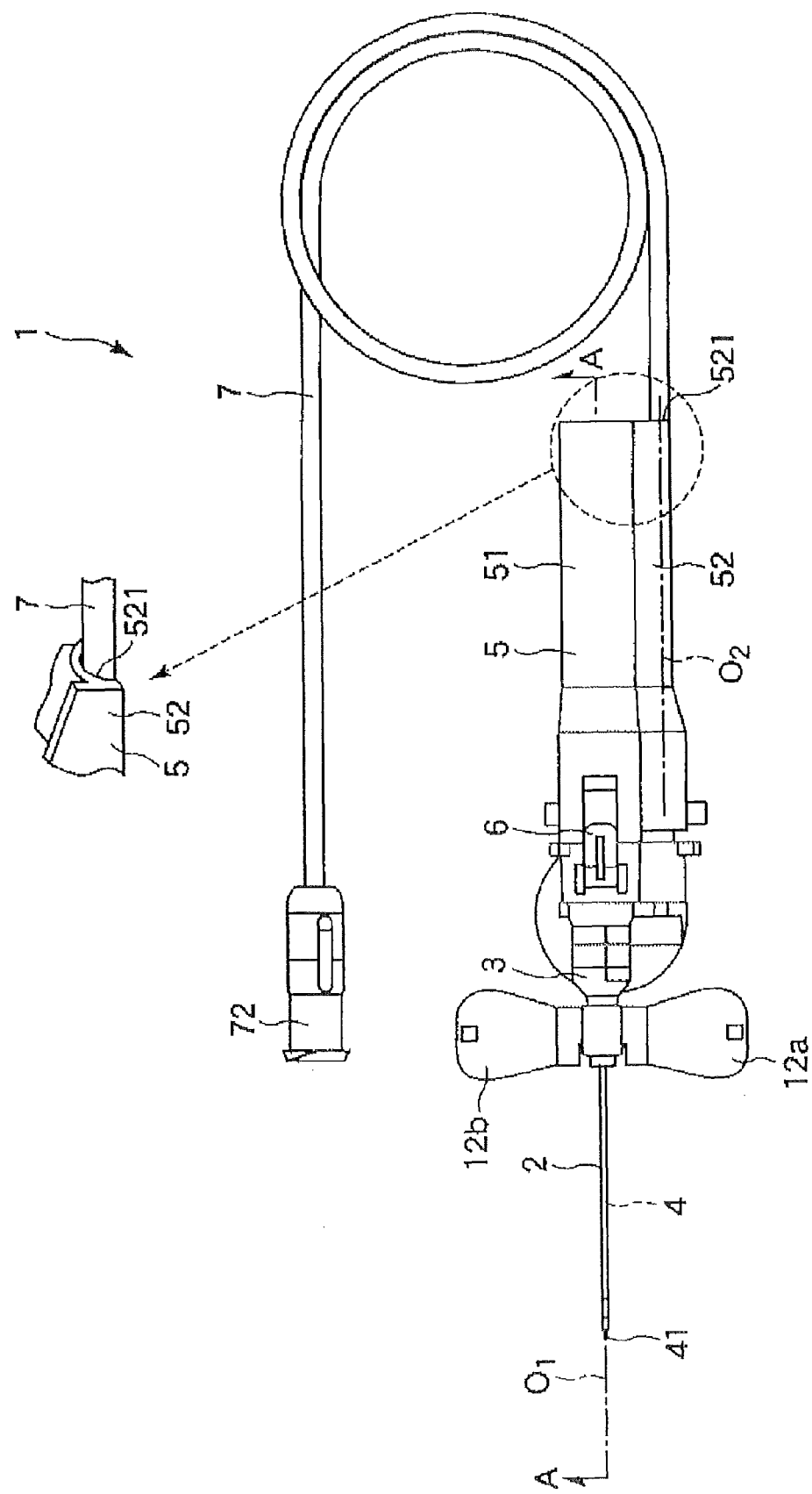
FIG. 1 is a plan view showing a first embodiment, in a case where the medical instrument according to the present invention is applied to an indwelling needle assembly.
Figure 2:
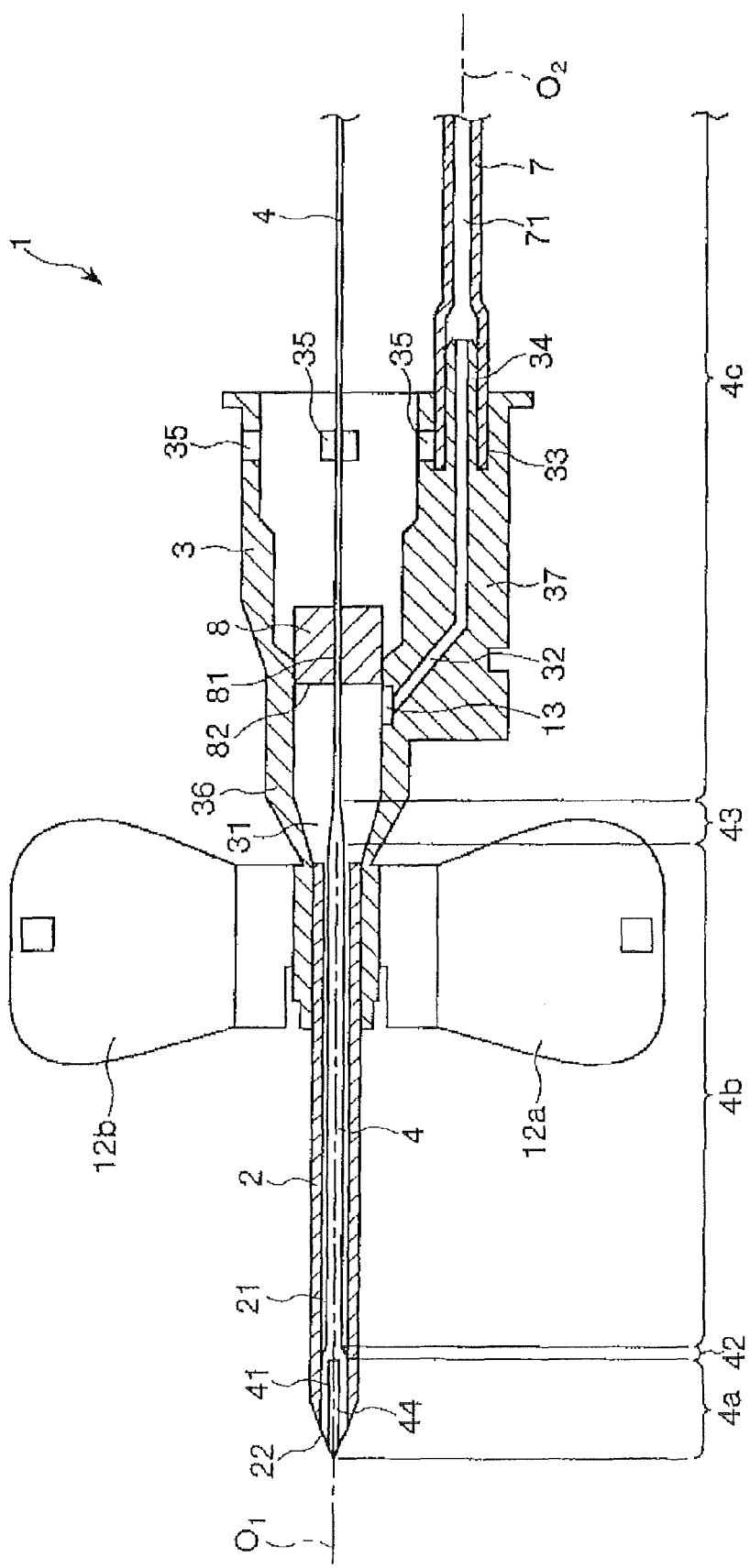
FIG. 2 is a sectional view showing an outer needle, an outer needle hub, an inner needle, and a tube in the indwelling needle assembly shown in FIG. 1.
Figure 3:
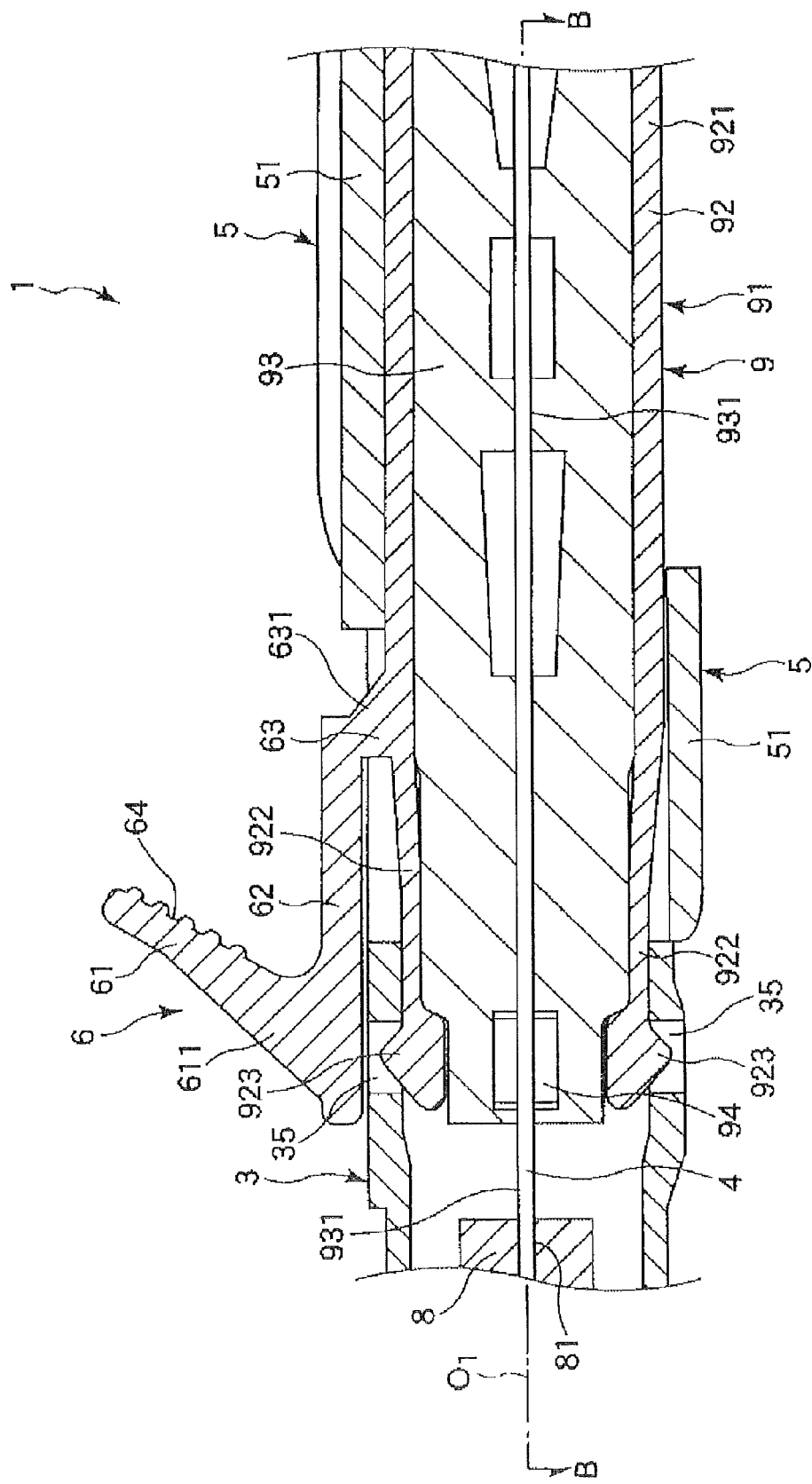
FIG. 3 is a sectional view taken along line A-A of FIG. 1.
Figure 4:
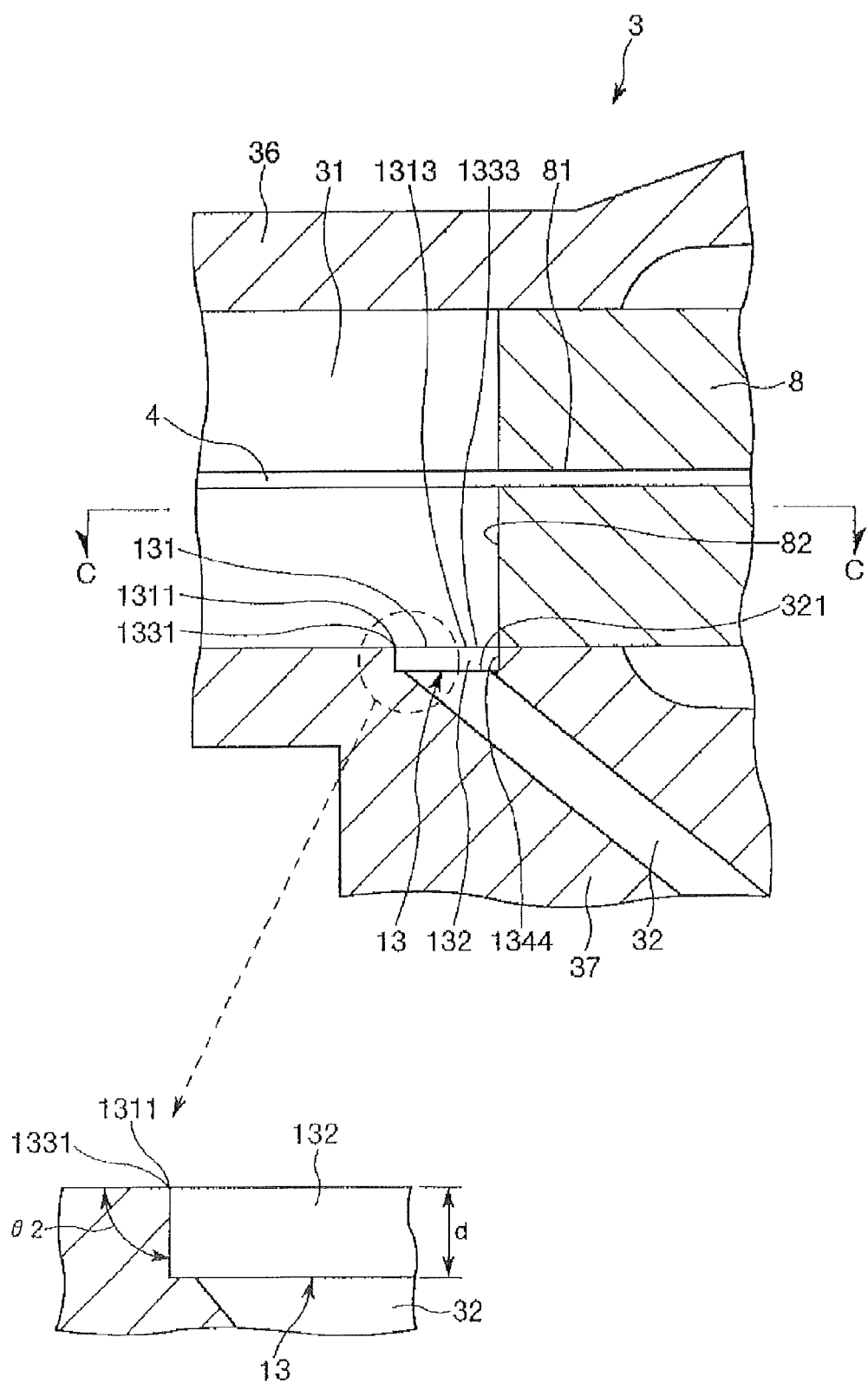
FIG. 4 is a sectional view showing a major part of the outer needle hub of the indwelling needle assembly shown in FIG. 1.
Figure 5:
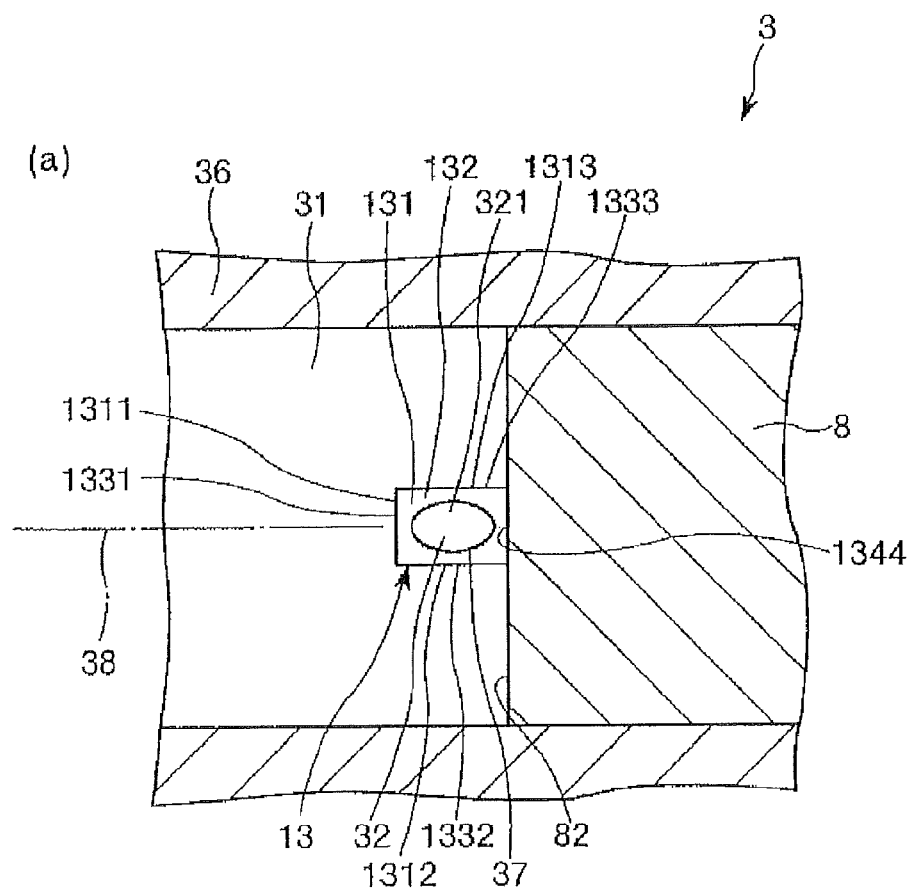
FIG. 5 are sectional views taken along line C-C of FIG. 4.
Figure 5:
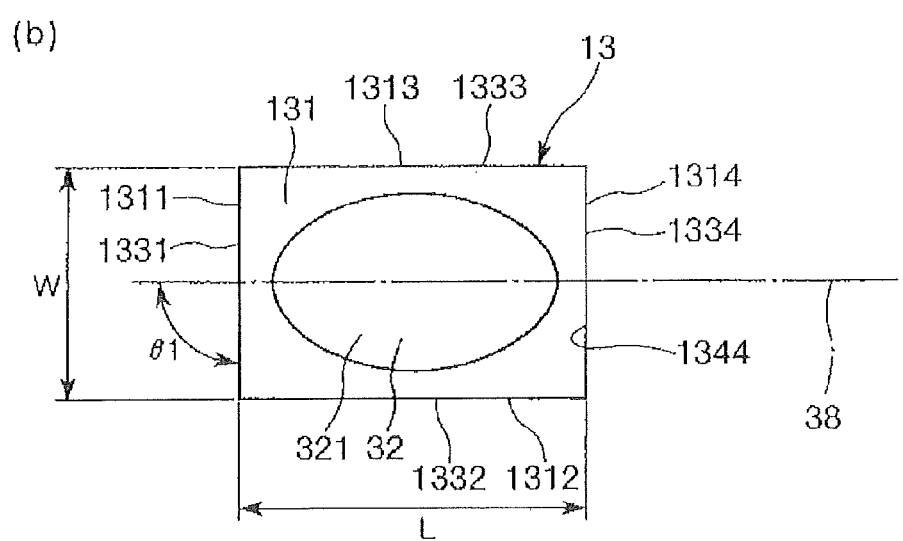
Figure 6:
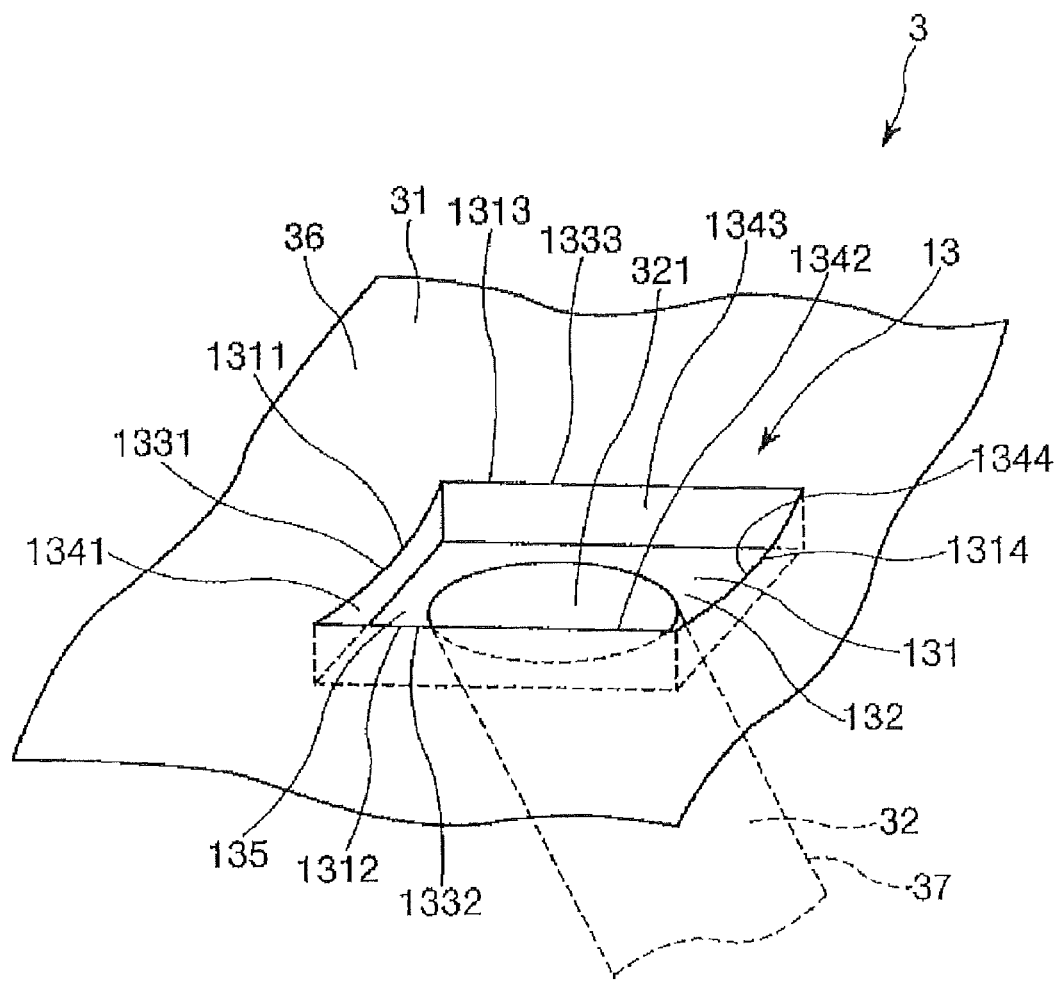
FIG. 6 is a perspective view showing a major part of the outer needle hub of the indwelling needle assembly shown in FIG. 1.
Figure 11:
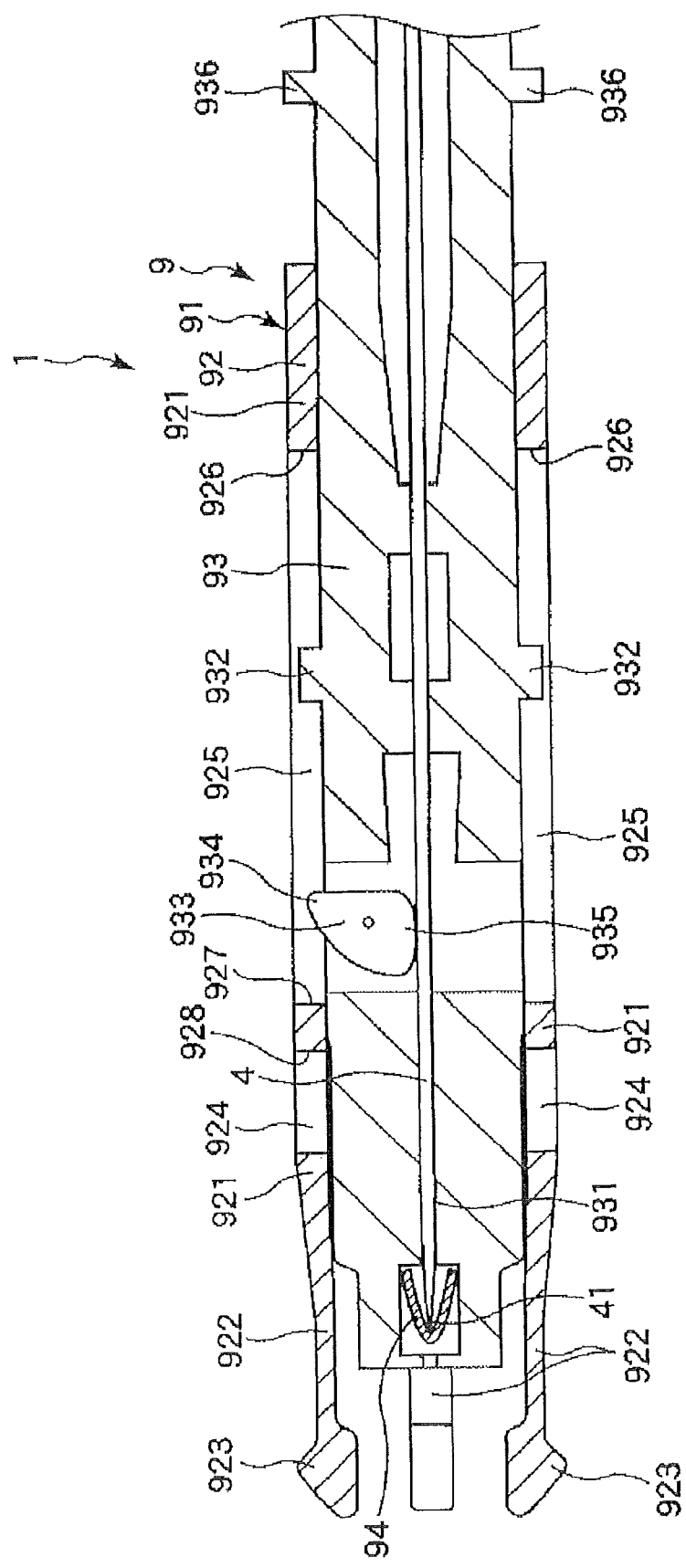
FIG. 11 is a sectional view taken along line B-B of FIG. 3.
Figure 12:
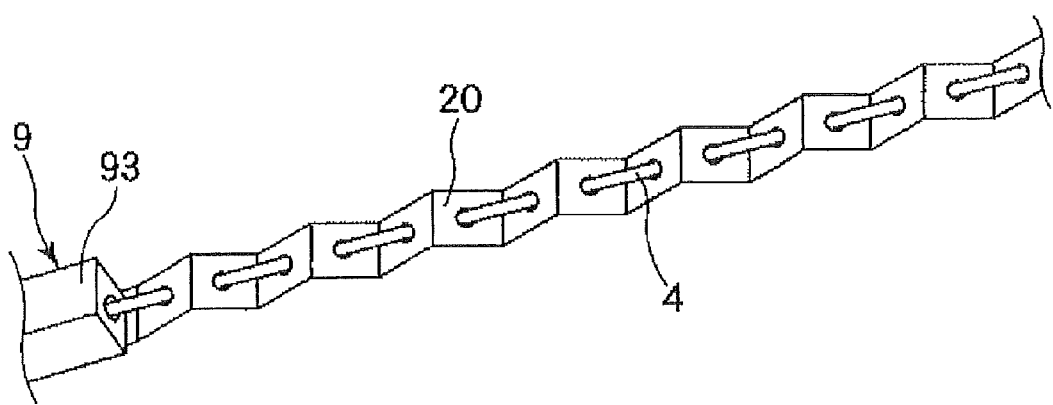
FIG. 12 is a perspective view of a connection member of the indwelling needle assembly shown in FIG. 1.
Figure 15:
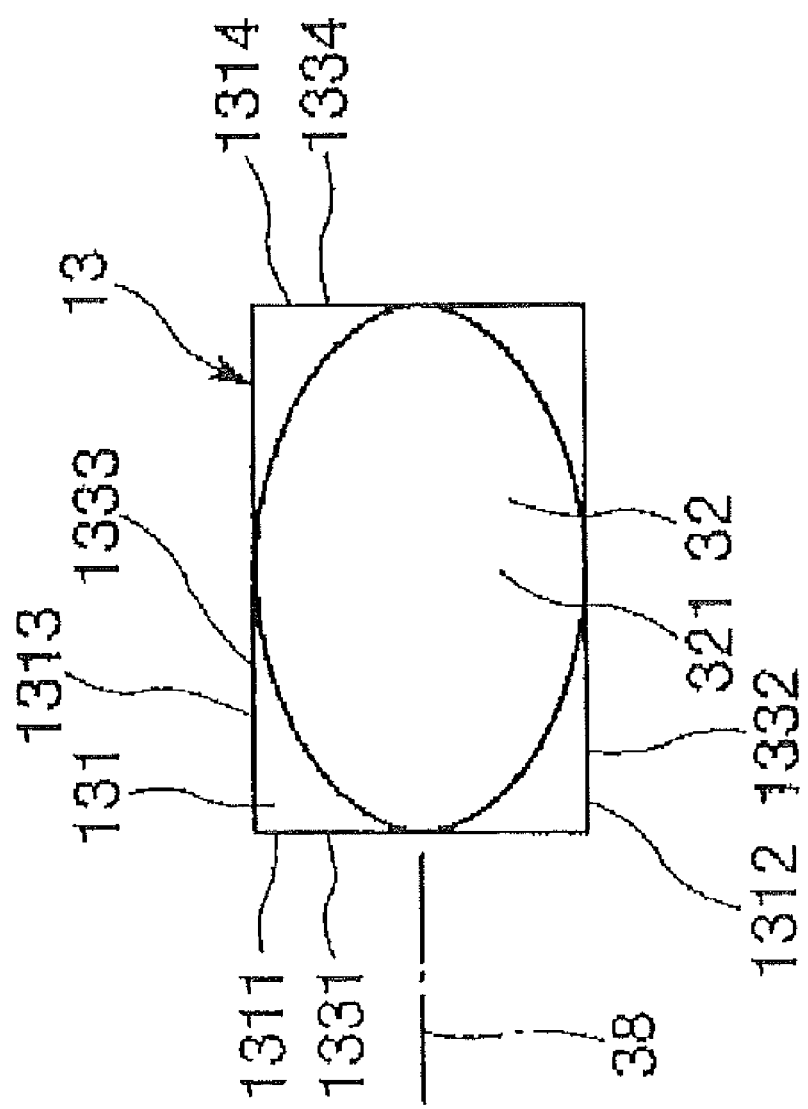
FIG. 15 is a plan view showing another configuration example of a step section of the outer needle hub in the indwelling needle assembly shown in FIG. 1.
Figure 16:
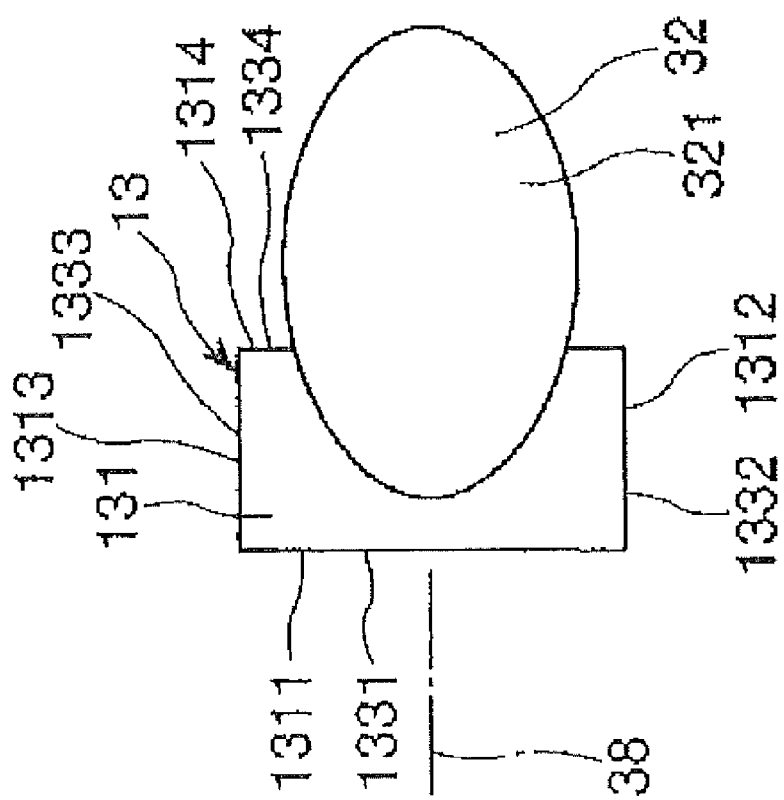
FIG. 16 is a plan view showing a further configuration example of the step section of the outer needle hub in the indwelling needle assembly shown in FIG. 1.
Figure 17:
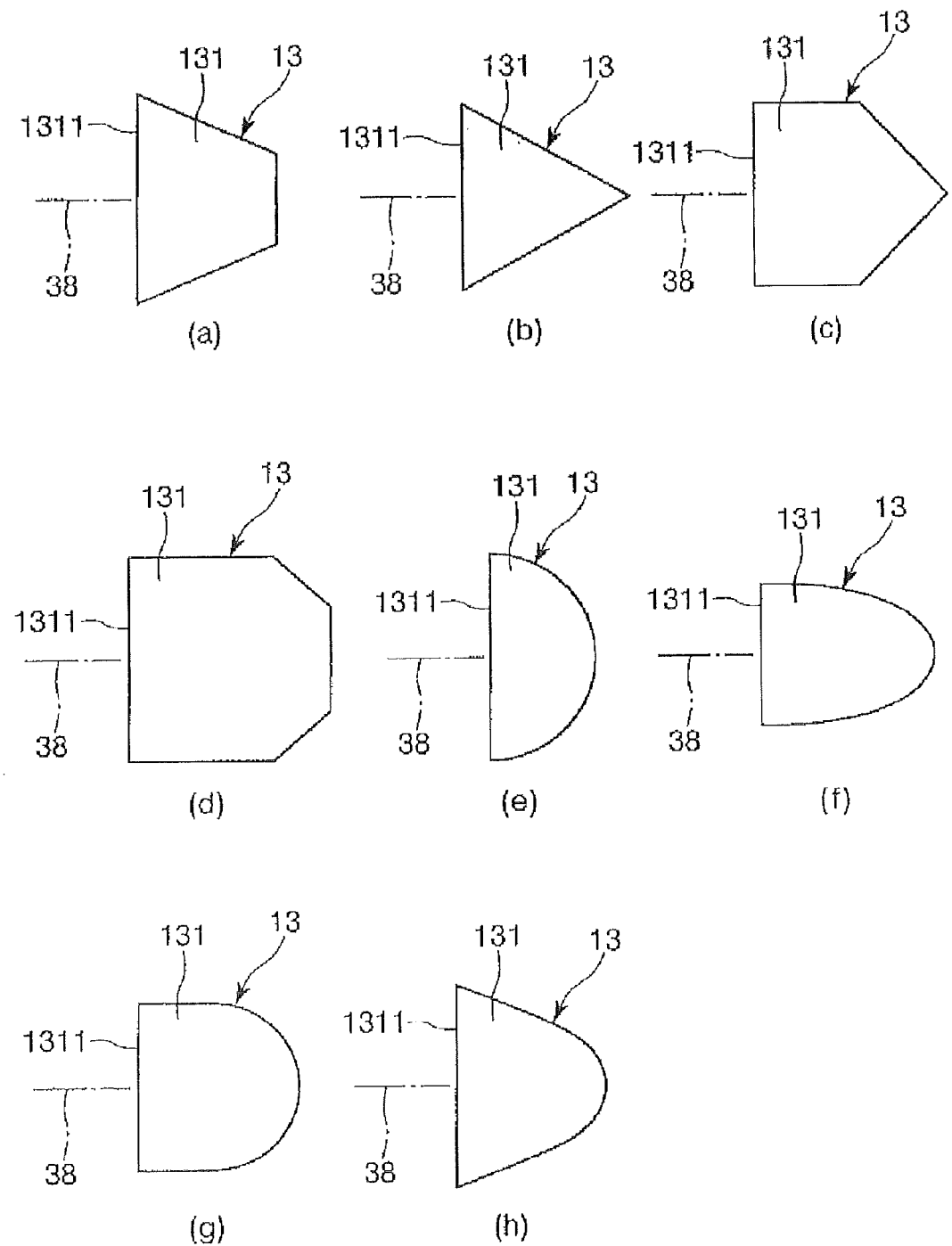
FIG. 17 are plan views showing other configuration examples of the step section of the outer needle hub in the indwelling needle assembly shown in FIG. 1.

FIG. 1 is a plan view showing a first embodiment, in a case where the medical instrument according to the present invention is applied to an indwelling needle assembly. FIG. 2 is a sectional view showing an outer needle, an outer needle hub, an inner needle, and a tube of the indwelling needle assembly shown in FIG. 1. FIG. 3 is a sectional view taken along line A-A of FIG. 1. FIG. 4 is a sectional view showing a major part of the outer needle hub of the indwelling needle assembly shown in FIG. 1. In addition, FIG. 5 shows sectional views taken along line C-C of FIG. 4, wherein FIG. 5(a) shows a major part of the outer needle hub, and FIG. 5(b) shows a step section. Further, FIG. 6 is a perspective view showing a major part of the outer needle hub of the indwelling needle assembly shown in FIG. 1. FIGS. 7 to 11 each are sectional views taken along line B-B of FIG. 3. FIG. 12 is a perspective view of a connection member of the indwelling needle assembly shown in FIG. 1, FIGS. 13 and 14 each are views illustrating operations of the indwelling needle assembly shown in FIG. 1. Lastly, FIGS. 15 to 17 are plan views showing other configuration examples of the step section of the outer needle hub, in the indwelling needle assembly shown in FIG. 1.

Incidentally, in the following descriptions, the right side in FIGS. 1 and 2 to 17 will be referred to as a "proximal" side, and the left side will be referred to as a "distal" side. In addition, in FIGS. 7 to 11, the inner needle hub 5 is omitted from illustration. Further, in the figures other than FIG. 2, the inner needle 4 is drawn as having a constant outside diameter.

In addition, in the following descriptions, in a situation where a liquid such as blood (body fluid), a medicinal liquid (infusion liquid), etc., flows from a side of the main pipe 36 toward a side of the side pipe 37 in the outer needle hub 3, the upstream side will be referred to as a "distal (side)" and the downstream side will be referred to as a "proximal (side)." Stated otherwise, in a situation where the liquid flows in a reverse direction to that mentioned above, the downstream side will be referred to as a "distal (side)" and the upstream side will be referred to as a "proximal (side)."

Further, in the following descriptions, the blood (body fluid), or the medicinal liquid (infusion liquid) and the like will be referred to generically simply as "liquid."

As shown in the drawings, the indwelling needle assembly (medical instrument) 1 includes a hollow outer needle (indwelling needle) 2, an outer needle hub 3 fixed to a proximal portion of the outer needle 2, an inner needle 4 inserted in the outer needle 2, an inner needle hub 5 fixed to a proximal portion of the inner needle 4, and a tube 7 connected to a proximal portion (or a side portion) of the outer needle hub 3 so that a lumen 71 thereof communicates with a lumen 21 of the outer needle 2. Configurations of these components will be described below.

As the outer needle 2, one having a certain degree of flexibility preferably is used. The material constituting the outer needle 2 is preferably a resin material, particularly a flexible (soft) resin material. Specific examples of such materials include fluoro-resins such as PTFE, ETFE, PFA, etc., olefin resins such as polyethylene, polypropylene, etc., and mixtures thereof, polyurethane, polyesters, polyamides, polyether nylon resins, and mixtures of olefin resins with ethylene-vinyl acetate copolymer.

The outer needle 2 may, wholly or partially, be formed so to enable the inside thereof to be visible. Further, the material constituting the outer needle 2 can be admixed with a radiopaque material, such as barium sulfate, barium carbonate, bismuth carbonate, tungstic acid, etc., thereby making the outer needle opaque to radiation.

The outer needle hub 3 is secured (fixed) to a proximal portion of the outer needle 2 in a liquid-tight fashion by a method such as caulking, fusing (heat fusing, microwave fusing, etc.), adhesion with an adhesive, etc.

The outer needle hub 3 includes a main pipe 36, and a side pipe (branch pipe) 37 having a branch flow path 32 branching from a flow path 31 of the main pipe 36. In the present embodiment, the flow path 31 and the branch flow path 32 are substantially circular in cross-section. The cross-sectional shape, however, is not limited to being substantially circular in shape and may, for example, be elliptical or the like.

As mentioned above, a proximal portion of the outer needle 2 is fixed to the distal side of the main pipe 36, and the flow path 31 communicates with the lumen 21 of the outer needle 2 on the distal side thereof. The flow path 31 (main pipe 36) is disposed so that an axis (center axis) thereof coincides substantially with the center axis $O_1$ of the outer needle 2 (i.e., so that the axis (center axis) thereof is substantially parallel to the center axis $O_2$ of a distal portion of the tube 7).

In addition, the outer needle hub 3 is formed with a recess 33 in a proximal portion of a portion (part) thereof, which is on the lower side in FIG. 2. At a bottom surface of the recess 33, a projection (connecting section) 34 is formed that projects toward the proximal side.

In FIG. 2, the side pipe 37 is disposed on the lower side of the main pipe 36. A distal end (one end) of the branch flow path 32 of the side pipe 37 opens into the flow path 31 of the outer needle hub 3, whereas a proximal end (other end) of the branch flow path 32 opens at the proximal end of the projection 34. The axis (center axis) of the branch flow path 32 (side pipe 37) is disposed such that a portion thereof ranging from the distal end to an intermediate portion is inclined at a predetermined angle relative to the axis of the flow path 31 (main pipe 36). Further, the branch flow path 32 (side pipe 37) is bent at an intermediate portion, and a portion thereof ranging from the intermediate portion to the proximal end is disposed substantially parallel to the axis of the flow path 31. Incidentally, the inclined portion of the branch flow path 32 is inclined so that the lower side of the branch flow path 32 is located on the proximal side as shown in FIG. 2. This ensures that liquid can flow through the branch flow path 32 smoothly. Also, the liquid can flow smoothly from the branch flow path 32 toward the distal side of the flow path 31, and can flow from the distal side of the flow path 31 into the branch flow path 32. Incidentally, the axis of the branch flow path 32 (side pipe 37) may also be set perpendicular to the axis of the flow path 31 (main pipe 36) (i.e., it is not critical that the branch flow path 32 be inclined relative to the axis of the flow path 31).

The projection 34 is inserted into a lumen 71 in a distal portion of the tube 7, whereby the distal portion (one end portion) of the tube 7 is connected to the side pipe 37 of the outer needle hub 3. This ensures that a liquid, such as a medicinal liquid (infusion liquid), can be supplied through the tube 7 into the outer needle 2 (outer needle hub 3).

In addition, as shown in FIG. 2, at lateral sides in the vertical direction of the outer needle hub 3, a pair of wings 12a and 12b are formed integrally with the outer needle hub 3. The wings 12a and 12b are flexible, and are configured so as to be openable and closeable by bending or curving portions of the wings 12a and 12b that are proximate adjoining regions thereof with the outer needle hub 3.

When the outer needle 2 and the inner needle 4 are made to puncture a blood vessel or the like, the wings 12a and 12b are placed in a closed state by pinching them together, so that the puncturing operation can be performed. In addition, instead of pinching the wings 12a and 12b, the inner needle hub 5 may be pinched by a thumb and a middle finger in order to perform a puncturing operation, and when the distal end of the outer needle 2 has reached the inside of the blood vessel, a finger holder section 6 (described later) may be pushed by an index finger in order to advance the outer needle hub 3, whereby only the outer needle 2 can be advanced into the blood vessel. When the outer needle 2 is set in an indwelling state, the wings 12a and 12b are placed in an opened state, and the wings 12a and 12b are fixed to the skin using a pressure sensitive adhesive tape or the like.

Further, the outer needle hub 3 is provided at a proximal portion thereof with four holes (recesses) 35, into which projections 923 of four projecting parts 922 of a protector cover 92 of a protector 9, to be described later, are inserted. The holes (recesses) 35 are arranged at regular angular intervals.

The inner needle 4, having a sharp needle tip 41 at the distal end thereof, is inserted into the outer needle 2. As shown in FIGS. 1 and 2, the indwelling needle assembly 1 is used in a state in which the inner needle 4 is inserted into the outer needle 2, and the inner needle hub 5 (described later) and the outer needle hub 3 are in contact with each other (i.e., a state in which the needle tip 41 protrudes from a tip opening 22 of the outer needle 2). Hereinafter, such a state will be referred to as an "assembled state."

The length of the inner needle 4 is set so that, in the assembled state, at least the needle tip 41 protrudes from the tip opening 22 of the outer needle 2.

The inner needle 4 may be either a hollow needle or a solid needle. In the case that the inner needle 4 is a solid needle, sufficient strength can be secured although the outside diameter thereof is small. Further, if the inner needle 4 is a solid needle, there is no danger that blood will remain inside the inner needle 4, or that blood might flow out therefrom, at a time of discarding the inner needle 4 after an operation has been completed. Thus, high safety is ensured.

In addition, in the case that the inner needle 4 is a hollow needle, it is ensured that when the inner needle 4 punctures a blood vessel, blood flows into the hollow portion of the inner needle 4, whereby flashback of the blood can be confirmed. In this connection, however, if the inner needle 4 is a solid needle, the blood flows into a gap formed between the inner needle 4 and the outer needle 2, which enables flashback of the blood to be confirmed more quickly.

Incidentally, the inner needle 4 can have a configuration of having both a hollow portion and a solid portion (for example, a configuration may be provided in which part of the lumen of a hollow needle is filled, so as to make the inner needle hollow at the distal side and solid at the proximal side thereof). In this case, when the entirety of the inner needle 4 is composed of a single member, the inner needle 4 can be reduced in cost.

Further, although the inner needle 4 may be constant in outside diameter, in the configuration shown in the figures, the inner needle 4 has a plurality of portions (in this embodiment, three portions) that differ in outside diameter. More specifically, the inner needle 4 includes a maximum outside diameter section 4a having a greatest outside diameter on a distal side (distal portion), a minimum outside diameter section 4c having a smallest outside diameter on a proximal side, and an intermediate outside diameter section 4b, the outside diameter of which is between that of the maximum outside diameter section 4a and the minimum outside diameter section 4c, and which is located between the sections 4a and 4b.

In addition, the inner needle 4 is provided with a first varying outside diameter section 42, which has a continuously varying outside diameter and which is located at a boundary portion between the maximum outside diameter section 4a and the intermediate outside diameter section 4b, and a second varying outside diameter section 43, which has a continuously varying outside diameter and which is located between the intermediate outside diameter section 4b and the minimum outside diameter section 4c.

While the outside diameter of the inner needle 4 may vary stepwise at each of the varying outside diameter sections 42 and 43, a configuration in which the outside diameter varies continuously (i.e., in a tapered manner) over such sections is advantageous for the following reason. In this manner, it is ensured that, when the inner needle 4 is pulled out from the outer needle 2, the varying outside diameter sections 42 and 43 can be prevented from becoming caught on a tip edge portion of a slit 81 formed in a seal member 8 (described later), the protector 9, or the like. Therefore, the operation of pulling the inner needle 4 out from the outer needle 2 can be carried out more smoothly and assuredly.

Incidentally, the varying outside diameter sections 42 and 43 may be formed at a time when the inner needle 4 is produced. Alternatively, steps, which are formed inevitably upon formation of a later-described groove 44, may be utilized.

Further, the outside diameter of the maximum outside diameter section 4a is set approximately equal to the inside diameter of the outer needle 2, so that the maximum outside diameter section 4a makes secure contact with the inner surface of the outer needle 2, in the condition where the inner needle 4 is inserted into the outer needle 2. The maximum outside diameter section 4a (distal portion) is provided, on an outer peripheral portion thereof, with the groove (flow path) 44, which is recessed along the longitudinal direction of the inner needle 4. The groove 44 permits the tip opening 22 of the outer needle 2 to communicate with the flow path 31 and the branch flow path 32 in the outer needle hub 3, in a condition where the inner needle 4 is inserted into the outer needle 2. The groove 44 also functions as a flow path for blood (body fluid) upon puncturing a blood vessel, for example. This enables flashback of blood to reliably be confirmed.

The material constituting the aforementioned inner needle 4 may be a metallic material such as, for example, stainless steel, aluminum or aluminum alloys, titanium or titanium alloys, etc.

The inner needle hub 5 is secured (fixed) to a proximal portion of the inner needle 4. The inner needle hub 5, in which the inner needle 4 is inserted, includes a protector containing section (connection member containing section) 51 for containing (enabling disposition of) the protector 9 (described later) and a connection member 20 therein in the assembled state. The inner needle hub 5 also includes a tube containing section 52, which is provided on a lateral side (lower side in FIG. 1) of the protector containing section 51, and in which a distal side of the tube 7 is contained (disposed) in the assembled state.

The protector 9 and the connection member 20 are movable relative to the protector containing section 51.

In addition, in the assembled state, the tube 7 is inserted into the inner needle hub 5, which prevents the tube 7 from obstructing operations of the indwelling needle assembly 1.

The tube containing section 52 is formed with a groove 521 therein, and the tube 7 is disposed inside the groove 521. The portion (part) defining (constituting) the groove 521 functions as a guide means for guiding the tube 7. The guide means, or the portion defining the groove 521, guides the tube 7 so that a center axis (axis) $O_2$ of a distal portion of the tube 7 will be substantially parallel to the longitudinal direction of the inner needle hub 5 (the center axis $O_1$ of the outer needle 2).

Thus, the tube 7 is configured so as to be connected to a proximal portion of the outer needle hub 3. Also, in the assembled state, the center axis $O_1$ of the outer needle 2 and the center axis $O_2$ of the distal portion of the tube 7 are substantially parallel to each other. In other words, the tube 7 projects in the proximal direction from the proximal end of the outer needle hub 3.

Further, when the tube 7 is detached from the inner needle hub 5 upon pulling the inner needle 4 out from the outer needle 2, the tube 7 can be detached easily and speedily by means of the groove 521 (through the groove 521).

Examples of methods for fixing the inner needle 4 to the inner needle hub 5 include fitting, caulking, fusing, adhesion with an adhesive, etc., as well as combinations of these methods. In addition, in the case that the inner needle 4 is hollow, sealing is required to prevent backward flowing blood, for example, upon puncturing a blood vessel, from flying out from the proximal end of the inner needle 4.

The inner needle hub 5 and the aforementioned outer needle hub 3 each preferably are formed of a transparent (colorless transparent), colored transparent or semi-transparent resin, so as to enable the insides thereof to be visible. This ensures that when the outer needle 2 has captured (i.e., has securely reached the inside of) a blood vessel, flashback of blood that flows in through the groove 44 of the inner needle 4, as described above, can be confirmed by visual observation. In addition, if the inner needle 4 is solid, the entire portion of the blood, which undergoes flashback under pressure inside the blood vessel, for example, flows back through the groove 44, so that better visibility and confirmation of flashback can be ensured.

Materials constituting the outer needle hub 3, the inner needle hub 5 and the wings 12a and 12b are not particularly limited. Examples of suitable materials include various resin materials including polyolefins such as polyethylene, polypropylene, ethylene-vinyl acetate copolymer, etc., polyurethane, polyamides, polyesters such as polyethylene terephthalate, polybutylene terephthalate, etc., polycarbonate, polybutadiene, polyvinyl chloride, and polyacetal.

The tube 7 is flexible, and a distal portion of the tube 7 is connected to a proximal portion of the outer needle hub 3, as mentioned above. A connector 72 is mounted to a proximal portion (other end portion) of the tube 7. The connector 72 is connected, for example, by means of a connector, which is attached to an end portion of an infusion line for supplying an infusion liquid (medicinal liquid) to be administered. The connector 72 may also be connected to a mouth portion (distal portion) of a syringe in which a medicinal liquid is contained, or the like.

Incidentally, the material constituting the tube 7 is not particularly limited. Examples of suitable materials include polyolefins such as polyethylene, polypropylene, ethylene-vinyl acetate copolymer, etc., polyvinyl chloride, polybutadiene, polyamides, polyurethane, polyesters, and so on.

In addition, the indwelling needle assembly 1 is provided, in the flow path 31 of the outer needle hub 3, with a cylindrical (block-like) seal member 8, which serves as a sealing means for sealing the flow path 31. The seal member 8 is disposed (fixed) in the flow path 31 of the main pipe 36, at a position on the proximal side relative to the branch flow path 32 (tip opening 321). In this embodiment, the seal member 8 is arranged in the vicinity of a step section 13, which will be described later.

The seal member 8 is formed with a hole or slit for insertion of the inner needle 4 therein, and which becomes closed when the inserted inner needle 4 is pulled out. In the present embodiment, a slit 81 is formed in a substantially central portion of the seal member 8. The slit 81 pierces through the seal member 8 in the longitudinal direction of the seal member 8.

The slit 81 is in the shape of a straight line segment. This enables the slit 81 to easily be brought from a closed state into an open state. Therefore, the inner needle 4 can be inserted smoothly into and passed through the seal member 8 (slit 81). More specifically, as will be described later, when the outer needle 2 is advanced using the inner needle 4 as a guide, frictional resistance between an outer surface of the inner needle 4 (minimum outside diameter section 4c) and an inner surface of the slit 81 can be reduced. Consequently, operability of the indwelling needle assembly 1 is enhanced when a puncturing operation is performed.

The seal member 8 also has a self-closing property, such that the slit 81 becomes closed by an elastic force (restoring force) of the seal member 8 itself when the inner needle 4, which is inserted in the slit 81 in the assembled state, is pulled out from the slit 81. This enables leakage of liquid from the proximal end of the outer needle hub 3 upon pulling out of the inner needle 4 to be prevented, and further maintains an aseptic condition inside the outer needle hub 3.

Further, as shown in FIG. 2, in the assembled state, the minimum outside diameter section 4c of the inner needle 4 is located in the slit 81. This ensures a small contact area between the outer surface of the minimum outside diameter section 4c and the inner surface of the slit 81, whereby frictional resistance between such surfaces can be kept small. In addition, the seal member 8 (slit 81) can be prevented from acquiring a semi-permanent deformation, which could lower the sealing performance thereof.

Examples of suitable materials constituting the seal member 8 include various elastic materials such as various rubber materials (particularly, vulcanized rubbers) such as natural rubber, isoprene rubber, butyl rubber, butadiene rubber, styrene-butadiene rubber, urethane rubber, nitrile rubber, acrylic rubber, fluoro-rubber, silicone rubber, etc., various thermoplastic elastomers based on urethane, polyester, polyamide, olefin, styrene or the like, as well as mixtures of the same.

In addition, the indwelling needle assembly 1 preferably is subjected to a friction-reducing treatment, for thereby reducing frictional resistance between the inner surface of the slit 81 and the outer surface of the inner needle 4.

Examples of friction-reducing treatments include a treatment in which a lubricant is applied to at least one of the inner surface of the slit 81 and the outer surface (outer peripheral surface) of the inner needle 4, and formation of a layer comprising a low-friction material (low-friction layer) on the inner surface of the slit 81.

Such a friction-reducing treatment makes it possible to securely reduce frictional resistance between the inner needle 4 and the seal member 8 during advancement of the outer needle 2 using the inner needle 4 as a guide. Consequently, the outer needle 2 can be moved smoothly, and when a puncturing operation is carried out, the indwelling needle assembly 1 is excellent in operability.

Further, the indwelling needle assembly 1 includes the protector 9, by which at least the needle tip 41 of the inner needle 4 is covered when the inner needle 4 has been pulled out from the outer needle 2.

Figure 7:
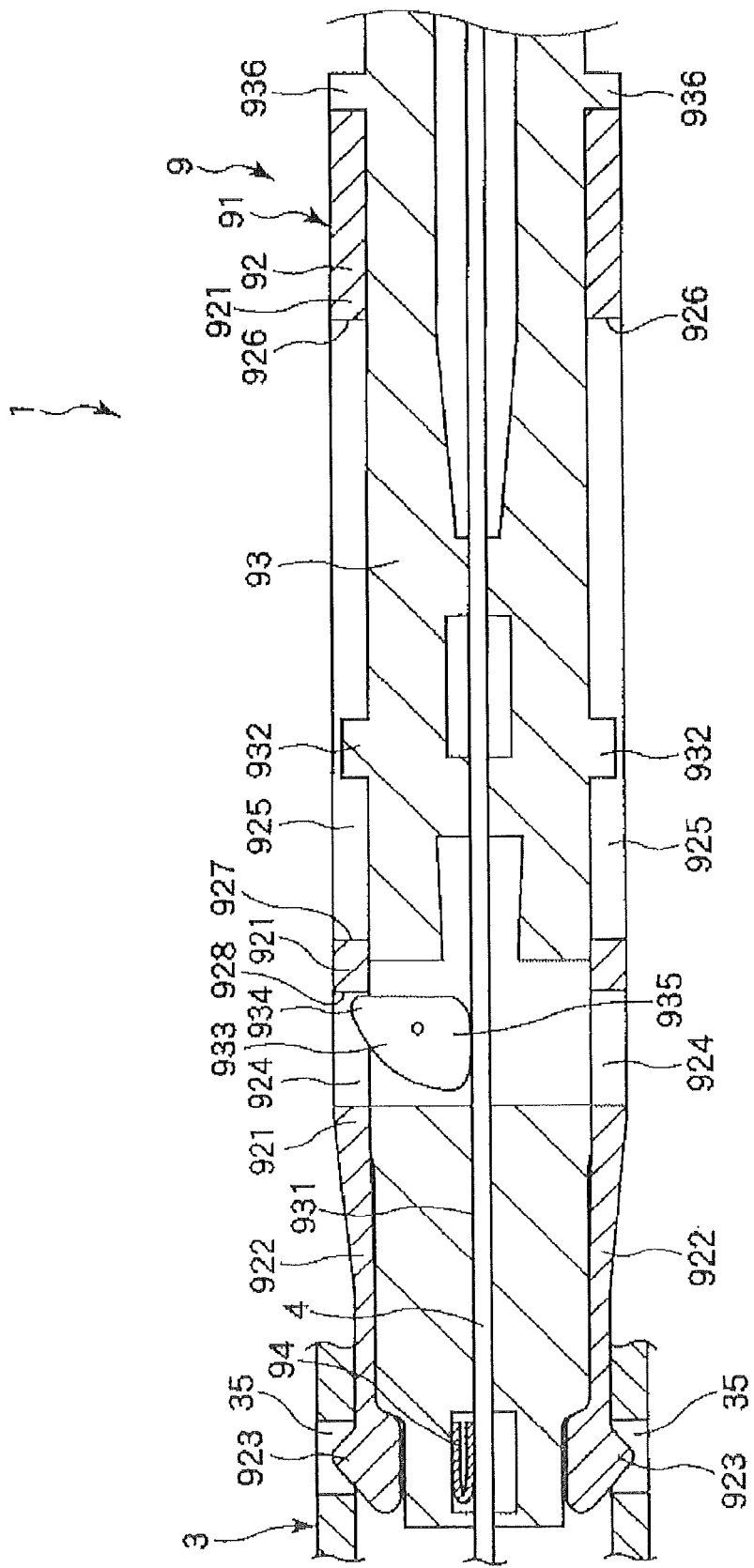
FIG. 7 is a sectional view taken along line B-B of FIG. 3.

The protector 9 is detachably connected to the outer needle hub 3. As shown in FIGS. 3 and 7, the protector 9 includes a protector body 91, and a shutter member (shutter means) 94 provided inside the protector body 91.

The protector body 91 includes the protector cover 92, and an inner member 93 that is inserted in the protector cover 92. The protector cover 92 and the inner member 93 are configured so as to be movable relative to each other. Further, the protector cover 92 and the inner member 93 can assume a state in which movement thereof is inhibited, as well as a state in which movement thereof is permitted.

The protector cover 92 includes a cover body section 921, which is pipe-like (tubular) in shape, and four projecting parts 922 formed at a distal portion of the cover body section 921, which project in the distal direction. Distal sides of the projecting parts 922 are inserted into a proximal portion of the outer needle hub 3. Each of the projecting parts 922 is provided at a distal portion thereof with a projection 923, which is inserted into the hole 35 formed in the proximal portion of the outer needle hub 3, and which becomes caught on an edge portion confronting the hole 35.

As shown in FIGS. 3 and 7, when the inner member 93 is inserted into the protector cover 92 and a distal portion of the inner member 93 is located at the region (position) of the projections 923 of the projecting parts 922 of the protector cover 92, the inner member 93 inhibits the projections 923 from being moved (displaced) along the direction of the center axis (axis) of the inner needle 4, whereby catching of the projections 923 on edge portions confronting the holes 35 (i.e., a condition in which the projections 923 are caught on the edge portions confronting the holes 35) is held (maintained). Consequently, the connected state of the protector 9 and the outer needle hub 3 is held.

Figure 10:
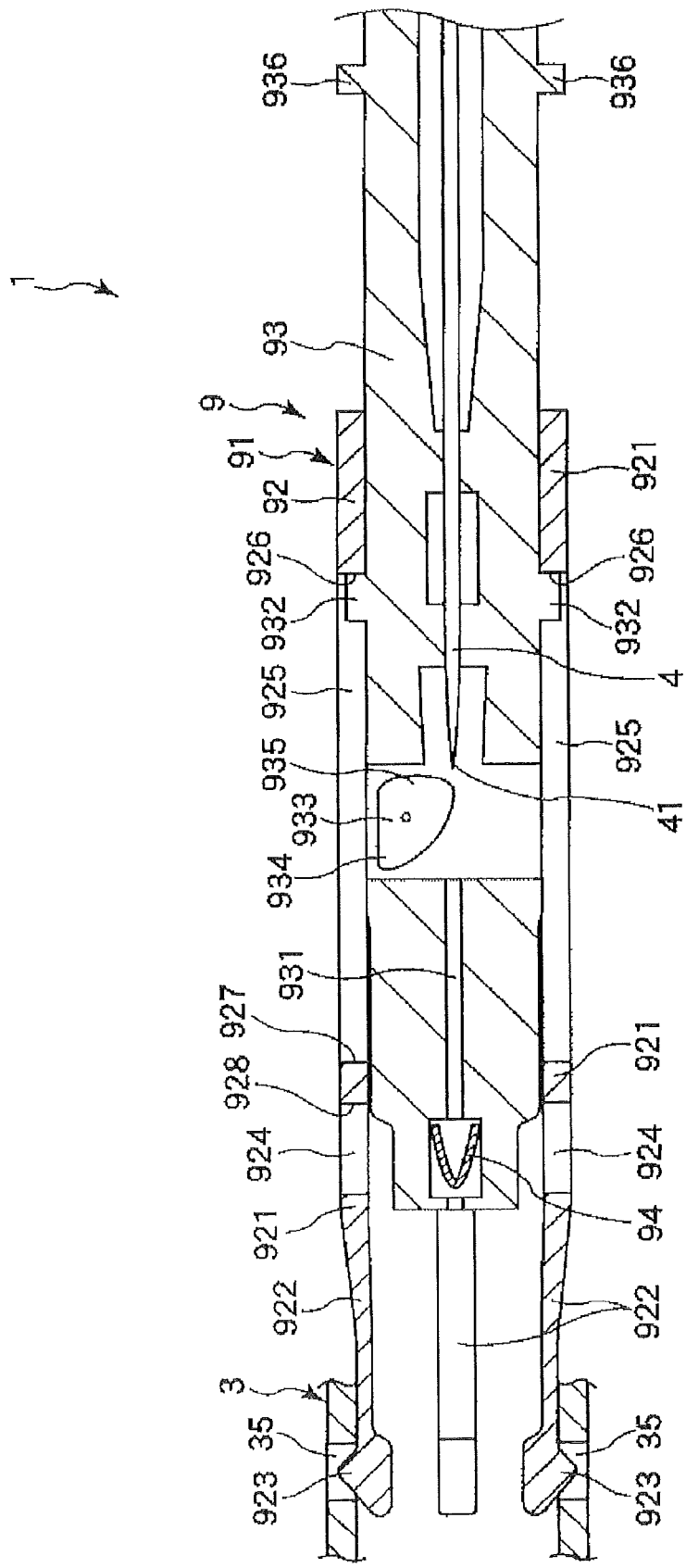
FIG. 10 is a sectional view taken along line B-B of FIG. 3.

Starting from this condition, when the inner member 93 is moved in the proximal direction relative to the protector cover 92 and until a distal portion of the inner member 93 reaches the proximal side of the projections 923 of the protector cover 92, as shown in FIG. 10, the projections 923 are capable of moving toward the center axis of the inner needle 4. In this condition, when the projector cover 92 is moved in the proximal direction relative to the outer needle hub 3, the projecting parts 922 are deformed (deflected) in directions approaching the center axis of the inner needle 4, whereby catching of the projections 923 on the edge portions confronting the holes 35 is released, and the protector 9 is released from the outer needle hub 3.

In addition, slots 924 and 925 are provided on both lateral sides of the cover body section 921 along the longitudinal direction thereof (in the longitudinal direction of the inner needle 4). The slots 924 are formed in a distal portion of the cover body section 921. Further, the slots 925 are formed on the proximal side relative to the slots 924. Lengths of the slots 925 in the longitudinal direction are greater than the lengths of the slots 924 in the longitudinal direction.

The material constituting the protector cover 92 is not particularly limited. For example, materials identical or similar to those mentioned above as materials for the outer needle hub 3 and the inner needle hub 5 can be used.

The inner member 93 is inserted into the protector cover 92. The inner member 93 is pipe-like (tubular) in shape. More specifically, the inner member 93 is provided at a central portion thereof with an inner needle passage 931, into which the inner needle 4 is inserted. The inner needle passage 931 pierces the inner member 93 from a proximal end toward a distal end of the inner member 93. The shutter member 94 is contained in an intermediate portion of the inner needle passage 931, which is located at a distal part of the inner member 93.

The material constituting the inner member 93 is not particularly limited. For example, materials identical or similar to those mentioned above as materials for the outer needle hub 3 and the inner needle hub 5 can be used.

The shutter member 94 is formed by bending an elastic (elastically deformable) belt-like plate member in a substantially V shape. With the opening angle thereof varied (opened and closed), the shutter member 94 can assume (can be deformed into) a first posture (the posture shown in FIGS. 3 and 7), thereby permitting the inner needle 4 to pass through (penetrate) the inner needle passage 931, and a second posture (the posture shown in FIG. 8), thereby inhibiting passage of the needle tip 41 of the inner needle 4.

As shown in FIGS. 3 and 7, when the inner needle 4 has completely passed through (penetrated) the inner needle passage 931, the shutter member 94 is contained therein in a folded state with a reduced opening angle, and therefore the shutter member 94 is in the first posture. In this condition, the protector 9 is movable along the longitudinal direction of the inner needle 4 (the direction of the center axis $O_1$ of the outer needle 2) relative to the inner needle 4 and the inner needle hub 5.

Figure 8:
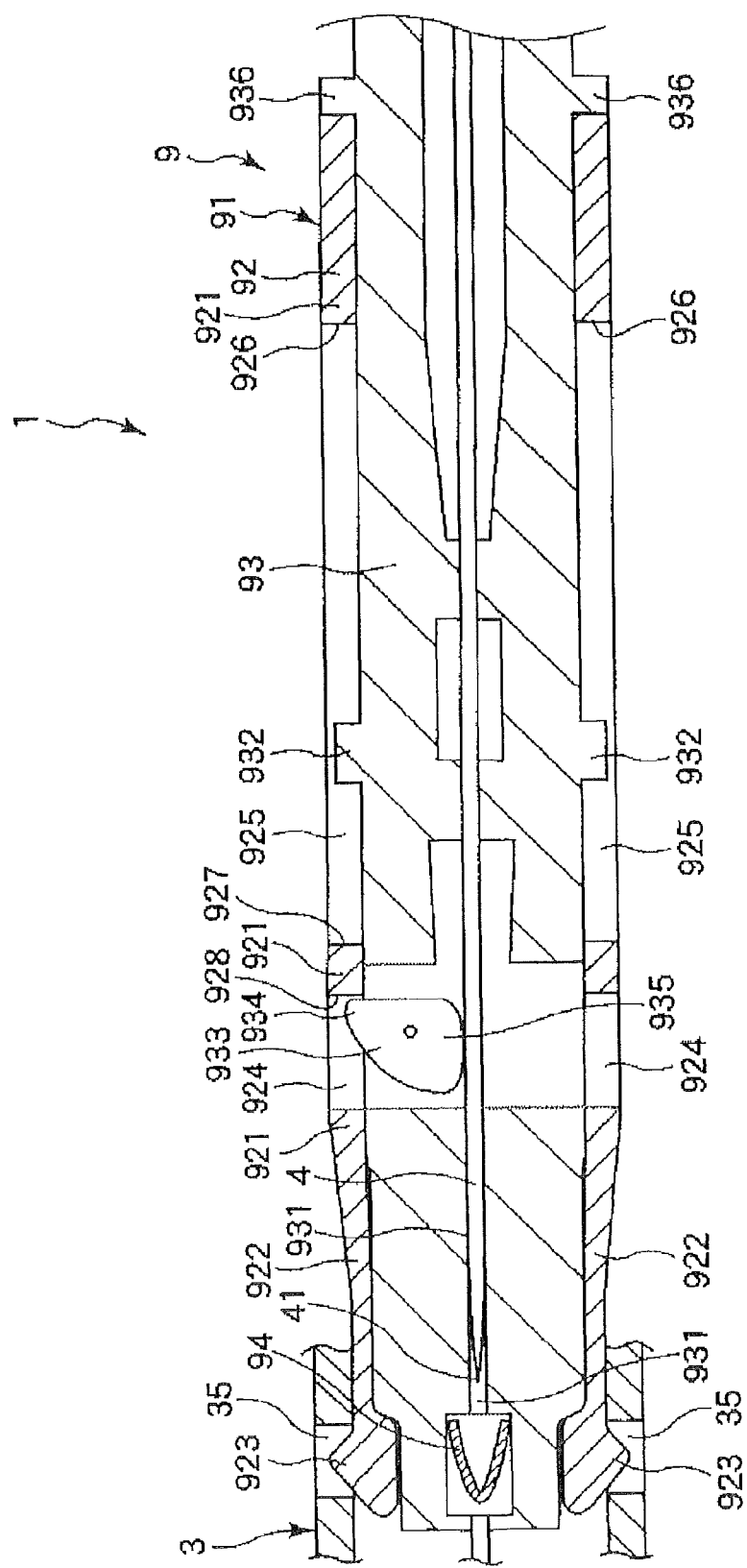
FIG. 8 is a sectional view taken along line B-B of FIG. 3.

Starting from this condition, when the inner needle hub 5 is moved in a proximal direction relative to the protector 9 and until the needle tip 41 of the inner needle 4 reaches the proximal side of the shutter member 94, as shown in FIG. 8, the shutter member 94 is opened under its own elastic force (restoring force), so as to assume the second posture, thereby shutting off and closing the inner needle passage 931. In this state, the shutter member 94 inhibits the needle tip 41 from moving (passing) in the distal direction beyond the shutter member 94.

The material constituting the shutter member 94 is not particularly limited, insofar as the material can inhibit passage of the needle tip 41 therethrough. Examples of suitable materials include various resin materials identical or similar to those mentioned above as materials for the outer needle hub 3 and the inner needle hub 5, and various metallic materials such as stainless steel, aluminum alloys, copper, titanium, etc.

Further, the thickness of the shutter member 94 is not particularly limited. For example, the thickness preferably is about 0.03 to 0.2 mm, and more preferably, about 0.04 to 0.1 mm.

In addition, a lubricant preferably is applied to a surface of the shutter member 94. This ensures that when the shutter member 94 is in the first posture, frictional resistance (sliding resistance) between the outer peripheral surface of the inner needle 4 and the shutter member 94 is reduced, so that the inner needle 4 can be moved more smoothly relative to the protector 9.

Incidentally, a part of the shutter member 94 may be fixed to the inner member 93 by a method such as, for example, embedding, fusing, adhesion with an adhesive, or the like. In addition, in the present invention, the configuration of the shutter member 94 is not limited to that shown in the drawings. The shutter member 94 may be of any shape or structure.

Further, the inner member 93 is provided, on both lateral sides of a central portion thereof, with projections 932, which are inserted into corresponding slots 925 of the protector cover 92.

This ensures that the inner member 93 can be prevented from rotating (turning) relative to the protector cover 92.

In addition, as shown in FIG. 10, when the inner member 93 is moved in the proximal direction relative to the protector cover 92, the projections 932 of the inner member 93 abut against edge portions 926 on the proximal side of the slots 925 in the protector cover 92. Consequently, the inner member 93 is inhibited from moving in the proximal direction relative to the protector cover 92. In this condition, when the inner member 93 is moved in the proximal direction relative to the protector cover 92, the inner member 93 and the protector cover 92 are moved integrally and in unison in the proximal direction. In addition, the inner member 93 can be prevented from slipping off (becoming released) from the protector cover 92.

Further, as shown in FIG. 7, a lock member 933 is rotatably disposed between the projection 932 and a lateral portion on the upper side of the inner member 93, at which the shutter member 94 is located (distal portion).

When the inner needle 4 is located at a portion corresponding to the lock member 933, for example, and when the inner needle 4 has passed completely through (penetrating) the inner needle passage 931, as shown in FIG. 7, a bottom portion (base end portion) 935 of the lock member 933 makes contact with the inner needle 4, and the lock member 933 is held in an orientation such that the tip portion 934 thereof is oriented away from the inner needle 4 (oriented upwardly as shown in FIG. 7) (the lock member 933 is inhibited from rotating). When the lock member 933 assumes this orientation, the tip portion 934 can make contact (engage) with a proximal-side edge portion 928 of the slot 924, and with a distal-side edge portion 927 of the slot 925.

Figure 9:
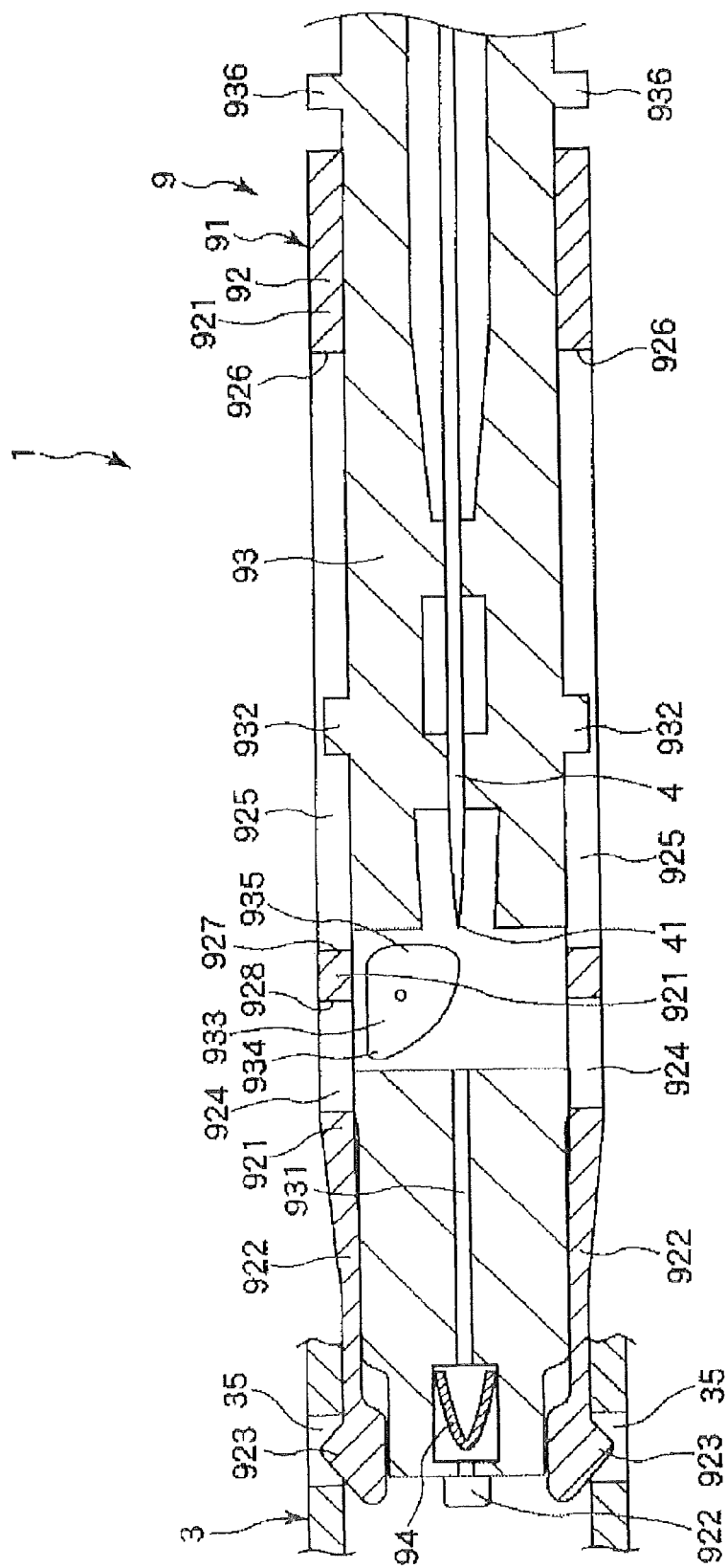
FIG. 9 is a sectional view taken along line B-B of FIG. 3.

In addition, when the inner needle 4 is located on the proximal side relative to the region of the lock member 933 (i.e., when the inner needle 4 is not located within the region of the lock member 933), as shown in FIG. 9, the lock member 933 can rotate, and the lock member 933 can assume an orientation such that no part thereof makes contact with either of the edge portions 927 and 928.

Further, the inner member 93 is provided, at both lateral sides of a proximal portion thereof, with ribs (flanges) 936, which can make contact with a proximal end face of the cover body section 921 of the protector cover 92.

In the assembled state, as shown in FIGS. 3 and 7, the inner member 93 is inserted into the protector cover 92, and a distal portion of the inner member 93 is located within the region of the projections 923 of the projecting parts 922 of the protector cover 92. This ensures that the latched state of the projections 923 on the edge portions confronting the holes 35 is held, and further that the connected state of the protector 9 and the outer needle hub 3 is maintained.

In addition, as a result of the ribs 936 of the inner member 93 being in contact with the proximal end of the cover body section 921 of the protector cover 92, the inner member 93 is inhibited from moving in the distal direction relative to the protector cover 92.

On the other hand, the inner needle 4 passes completely through the inner needle passage 931, and as mentioned above, the lock member 933 is held in an orientation such that the tip portion 934 thereof is oriented away from the inner needle 4 (oriented toward the upper side as shown in FIG. 7). The tip portion 934 of the lock member 933 is located in the slot 924, and with the tip portion 934 making contact with the proximal-side edge portion 928 of the slot 924, the inner member 93 is prevented from moving in the proximal direction relative to the protector cover 92.

This ensures that the inner member 93 and the protector cover 92 are moved integrally and in unison. Consequently, the protector 9 and the outer needle hub 3 also are moved together integrally.

According to the protector 9, as described above, after use thereof, the needle tip 41 of the inner needle 4 can be covered speedily and safely through an easy operation. In addition, the operation of the shutter member 94 ensures that the needle tip 41, once covered, cannot protrude from the distal end of the protector body 91 (inner member 93) of the protector 9. Therefore, when discarding the inner needle 4 or the like, or in other similar situations, an accident, in which a worker or similar person sticks his or her finger or the like with the needle tip 41 by mistake, is prevented from occurring, and high safety is ensured.

Further, as shown in FIG. 12, the indwelling needle assembly 1 has a connection member 20, which functions as a slip-off preventive means for preventing the protector 9 from slipping off from the needle tip 41 of the inner needle 4 when the needle tip 41 is covered by the protector 9, and which also functions as a connection means for connecting the protector 9 and the inner needle hub 5 to each other.

The connection member 20 is configured so as to connect the inner member 93 of the protector 9 and the inner needle hub 5 to each other. This ensures that when the inner needle hub 5 is moved in the proximal direction, the inner member 93 (protector 9) is pulled (moved), by way of the connection member 20, in the proximal direction.

In addition, the connection member 20 is bellows-like in form, and therefore is capable of being contracted and expanded. The connection member 20 has a length such that, in its maximally expanded (fully expanded) state, the needle tip 41 of the inner needle 4 is located on the proximal side relative to the lock member 933, and the needle tip 41 is contained within the inner member 93 (the needle tip 41 cannot slip off from the inner needle 93).

Thus, the connection member 20 connects the inner member 93 and the inner needle hub 5 to each other. Further, in its maximally expanded state, the length of the connection member 20 is such that the needle tip 41 is contained within the inner member 93. Therefore, the protector 9 is prevented securely from slipping off from the inner needle hub 5 and the needle tip 41. Accordingly, a condition in which the protector 9 covers the needle tip 41 can reliably be maintained. As a result, upon discarding the inner needle 4 or in other similar situations, an accident, in which a worker or similar person sticks his or her finger or the like with the needle tip 41 by mistake, is capable of being prevented, and high safety is ensured.

Further, in the assembled state, the connection member 20 is contracted, or folded, whereas the connection member 20 is expanded, or spread, in a condition where the inner needle 4 has been pulled out of the outer needle 2 and the needle tip 41 is covered by the protector 9.

The aforementioned connection member 20 is contracted in the assembled state, and in the contracted state, is contained in the inner needle hub 5. This ensures that the connection member 20 does not obstruct a puncturing operation, so that operability of the indwelling needle assembly 1 can be enhanced. Further, an additional merit is that the indwelling needle assembly 1 can be reduced in size.

In addition, the inner needle 4 penetrates through the connection member 20, both when the connection member 20 is in the contracted state, as well as when the connection member 20 is in the expanded state. This ensures that the inner needle 4 functions to guide the connection member 20 during expansion and contraction of the connection member 20. Therefore, for example, when the indwelling needle assembly 1 is arranged in the assembled state (i.e., when the indwelling needle assembly 1 is manufactured), the connection member 20 can reliably be prevented from being contracted in an unintended state, and more specifically, from being contracted without being contained within the inner needle hub 5.

Moreover, the connection member 20 has a self-restoring property (restoring force), which tends to return the connection member 20 to its natural state. Therefore, when the connection member 20 is contracted shorter than its natural state, the connection member 20 functions as a biasing means, and is biased in the expanding direction by the restoring force thereof. On the other hand, when the connection member 20 is expanded longer than its natural state, the connection member 20 functions as a biasing means, and is biased in the contracting direction. The term "natural state" implies a state in which no external forces are exerted on the connection member 20.

As shown in FIG. 3, the protector cover 92 of the protector 9 is formed (provided) with a projecting finger holder part (tab) 6, which is pushed by a finger in order to move the outer needle 2 in the distal direction relative to the inner needle 4. The protector cover 92 and the finger holder part 6 are formed integrally. Further, the finger holder part 6 projects in an upward direction.

In addition, in the present embodiment, the finger holder part 6 is formed at a distal portion of the cover body section 921 of the protector cover 92. The finger holder part 6 has a shape obtained by bending a plate body. More specifically, the finger holder part 6 is composed of an inclined section (inclined plate) 61, which is disposed on the distal side relative to the cover body section 921, and which is inclined toward the proximal side, a base section fixed to a distal portion of the cover body section 921, and a connecting section (connecting plate) 62 that interconnects the inclined section 61 and the base section 63. Further, a proximal-side surface of the inclined section 61 constitutes a finger holder surface 64.

With the finger holder part 6, during a puncturing operation when the outer needle 2 is moved in the distal direction relative to the inner needle 4, a finger is inserted between the finger holder surface 64 (inclined section 61) and the connecting section 62, the finger is placed on the finger holder surface 64, and the finger holder part 6 can be pushed in the distal direction while lifting (in a manner of lifting) the finger holder part 6 in the projecting direction thereof (i.e., upwardly in FIG. 3). This ensures that the outer needle 2 is capable of moving in a straight line along the center axis $O_1$, that is, along the direction of the center axis $O_1$, without causing the outer needle 2 to bend. Consequently, the outer needle 2 can be moved (advanced) smoothly, and excellent operability is ensured.

In addition, the finger holder surface 64 of the finger holder part 6 is formed with a certain degree of roughness (for example, a plurality of ribs arranged side by side along an up-down direction of the finger holder surface 64), which acts as a finger anti-slip means. This prevents the finger from slipping off during movement of the outer needle 2 in the distal direction, by pushing the finger holder part 6 with the finger.

Further, the finger holder part 6 has a reinforcement part for restraining deflection when the finger holder part 6 is pushed with a finger. The reinforcement part is composed of a rib 611 formed on a side of the inclined section 61, which is opposite to the finger holder surface 64, and a rib 631 formed on the base section 63.

Incidentally, the protector cover 92 and the finger holder part 6 may be formed as separate members, which are joined to each other. In this case, the material constituting the finger holder part 6 is not particularly limited. For example, materials can be used that are identical or similar to those mentioned above as materials for the outer needle hub 3 and the inner needle hub 5. In addition, the finger holder part 6 may project in another direction (for example, toward a lateral side). Further, the finger holder part 6 may be formed on another part (member) so as to project therefrom, for example, on the outer needle hub 3.

Meanwhile, as shown in FIGS. 2 to 6, the outer needle hub 3 of the indwelling needle assembly 1 has a step section 13, which acts as a speed reducing means for reducing the speed, in the axial direction (longitudinal direction) of the flow path 31 of the main pipe 36, of a portion of the liquid that flows in the flow path 31 (main pipe 36). The portion of the liquid forms a portion thereof that flows along the portion of the inner surface of the main pipe 36, which is located on the side on which the branch flow path 32 is located.

The step section 13 has an opening 131, which is formed in the inner surface of the main pipe 36. The opening 131 is disposed at a position corresponding to the distal end on the main pipe 36 side of the branch flow path 32, or at the tip opening 321. The step section 13 forms a space 132 between the opening 131 and the tip opening 321 of the branch flow path 32. The flow path 31 and the branch flow path 32 communicate with each other via the opening 131 and the space 132.

Incidentally, in the present embodiment, the branch flow path 32 is substantially circular in cross-section. Therefore, the tip opening 321 of the branch flow path 32 is substantially elliptical in shape, wherein the length of the minor axis of the tip opening 321 is equal to the diameter of the branch flow path 32.

The opening 131 has a profile including a rectilinear portion 1311, which is substantially perpendicular to the axis (center axis) 38 of the flow path 31 (main pipe 36). The rectilinear portion 1311 is located on the distal side (the upstream side with respect to the flow of liquid from the side of the main pipe 36 to the side of the side pipe 37). In the present embodiment, the opening 131 is tetragonal (rectangular) in shape, such that the side (edge) of the tetragon, which is located on the distal side, forms the rectilinear portion 1311. As a result of an edge (edge portion) 1331, which confronts the rectilinear portion 1311 of the opening 131 of the step section 13, the speed of liquid flowing toward such a portion (edge 1331) can be reduced. More specifically, the liquid is temporarily (momentarily) stopped at the edge 1331 due to surface tension. This ensures that it is possible to prevent bubbles (air) from remaining in the flow path 31 of the main pipe 36 in the vicinity of the tip opening 321 of the side pipe 37, at a time when liquid is allowed to flow therethrough, as will be described later.

In addition, as viewed in plan (in FIG. 5), preferably, the rectilinear portion 1311 of the opening 131 is located on the distal side relative to the distal end of the tip opening 321, or is coincident (in contact) with the distal end of the tip opening 321. In the configuration shown in the figure, the rectilinear portion 1311 is located on the distal side relative to the distal end of the tip opening 321.

Incidentally, the angle $\theta 1$ formed between the rectilinear portion 1311 (edge 1331) and the axis 38 preferably is 90°, similar to the configuration shown in the figures.

In addition, the step section 13 has an edge with a predetermined angle at the edge (edge portion) 1331 thereof. More specifically, the edge 1331 of the step section 13 is not rounded but is sharp. The edge angle $\theta 2$ of the edge 1331 preferably is not more than 90°, and more preferably, is about 60° to 90°. This ensures that the speed of the liquid can be reduced more reliably.

Further, it is preferable that the edges of the step section 13, at edges (edge portions) 1332 and 1333 thereof, confront the two (pair of) rectilinear portions 1312 and 1313, which are disposed on the upper and lower sides in FIG. 5 of the rectilinear portion 1311 of the opening 131, similar to the edge 1331. This ensures that the speed of the liquid can be reduced more assuredly.

In addition, an edge may either be formed or not formed at the edge (edge portion) 1334 of the step section, which confronts a proximal-side rectilinear portion 1314 of the opening 131. In the present embodiment, a proximal side surface 1344 of the step section 13, and a distal end surface 82 of the seal member 8 form a stepless continuous plane (surface). This ensures that liquid flows smoothly along the surfaces between the side surface 1344 of the step section 13 and the distal end surface 82 of the seal member 8. Incidentally, the rectilinear portion 1314 (edge portion 1334) of the opening 131 may be located on the distal side relative to the distal end surface 82 of the seal member 8.

Further, in plan view (in FIG. 5), the opening 131 of the step section 13 includes the tip opening 321 of the branch flow path 32. In the configuration shown in the drawings, portions of the opening 131, which reside respectively on the distal side, the proximal side, the upper side in FIG. 5, and the lower side in FIG. 5, are each greater than the tip opening 321. More specifically, concerning the opening 131, the rectilinear portion 1311 (edge 1331) constituting the distal end, the rectilinear portion 1314 (edge 1334) constituting the proximal edge, the rectilinear portion 1313 (edge 1333) constituting the upper-side end in FIG. 5, and the rectilinear portion 1312 (edge 1332) constituting the lower-side end in FIG. 5 are located respectively on the distal side, the proximal side, the upper side in FIG. 5, and the lower side in FIG. 5, relative to the tip opening 321. This makes it possible to securely prevent bubbles from remaining in the portion of the flow path 31 of the main pipe 36 that is in the vicinity of the tip opening 321 of the side pipe 37.

The size of the opening 131 is not particularly limited. The size is set appropriately according to various conditions, such as the diameter of the flow path 31 (the inside diameter of the main pipe 36), the diameter of the branch flow path 32 (the inside diameter of the side pipe 37), the inclination angle of the branch flow path 32 relative to the flow path 31, etc. A preferable range for the size of the opening 131 is discussed below.

The width (the length of the rectilinear portion 1311 (the edge 1331)) W of the opening 131 is not particularly limited. Preferably, the width W is not more than 3 mm, more preferably is about 1 to 3 mm. This ensures that the speed of liquid can be reduced appropriately, and it is possible to more securely prevent the problem of bubbles remaining in the portion of the flow path 31 of the main pipe 36 that is in the vicinity of the opening 321 at the distal end (tip) of the side pipe 37.

In addition, the length L (i.e., the length of the rectilinear portions 1312, 1313 (edges 1332, 1333)) of the opening 131 in the axial direction of the main pipe 36 is not particularly limited. The length L preferably is about 0.1 to 3 mm, and more preferably, about 0.5 to 2 mm. This ensures that the speed of the liquid can be reduced appropriately, and it is possible to more securely prevent the problem of bubbles remaining in the portion of the flow path 31 of the main pipe 36 that is in the vicinity of the tip opening 321 of the side pipe 37.

Further, the height (depth) d of the step section 13 is not particularly limited (as shown in the drawings, the height d is comparatively short, but it may be comparatively long). Preferably, the height (depth) d is about 0.05 to 2 mm, and more preferably, about 0.1 to 1 mm. This makes it possible to more securely prevent the problem of bubbles remaining in the portion of the flow path 31 of the main pipe 36 that is in the vicinity of the tip opening 321 of the side pipe 37.

In addition, in the configuration shown in the drawings, although the bottom surface 135 of the step section 13 is a flat surface, the invention is not limited to such a configuration. For example, the bottom surface 135 may be a curved surface, and more specifically, a curved concave surface or a curved convex surface.

Further, for example, it is preferable that the side surfaces 1341, 1342 and 1343, and the bottom surface 135 of the step section 13, particularly, the distal-side side surface 1341, are subjected to a hydrophobicity-imparting treatment (water repellency-imparting treatment) so as to be higher in hydrophobicity (water repellency) than other parts. This makes it possible to cope with higher liquid speed, higher liquid pressure, and the like, and to reduce the size of the step section 13. Thus, the degree of freedom in designing also is enhanced. In other words, it is possible to more securely reduce the speed of liquid, and to more securely prevent the problem of bubbles remaining in the portion of the flow path 31 of the main pipe 36 that is in the vicinity of the tip opening 321 of the side pipe 37.

The hydrophobicity-imparting treatment is not particularly limited. Exemplary methods therefor include formation of a fluoro-resin film by a treatment with fluorine, or the like.

Next, operations of the indwelling needle assembly 1, and more specifically, operations (and effects) of the step section 13, will be described below with reference to FIGS. 13 and 14, in comparison with a conventional indwelling needle assembly, in which the outer needle hub thereof is not provided with a step section.

Figure 20:
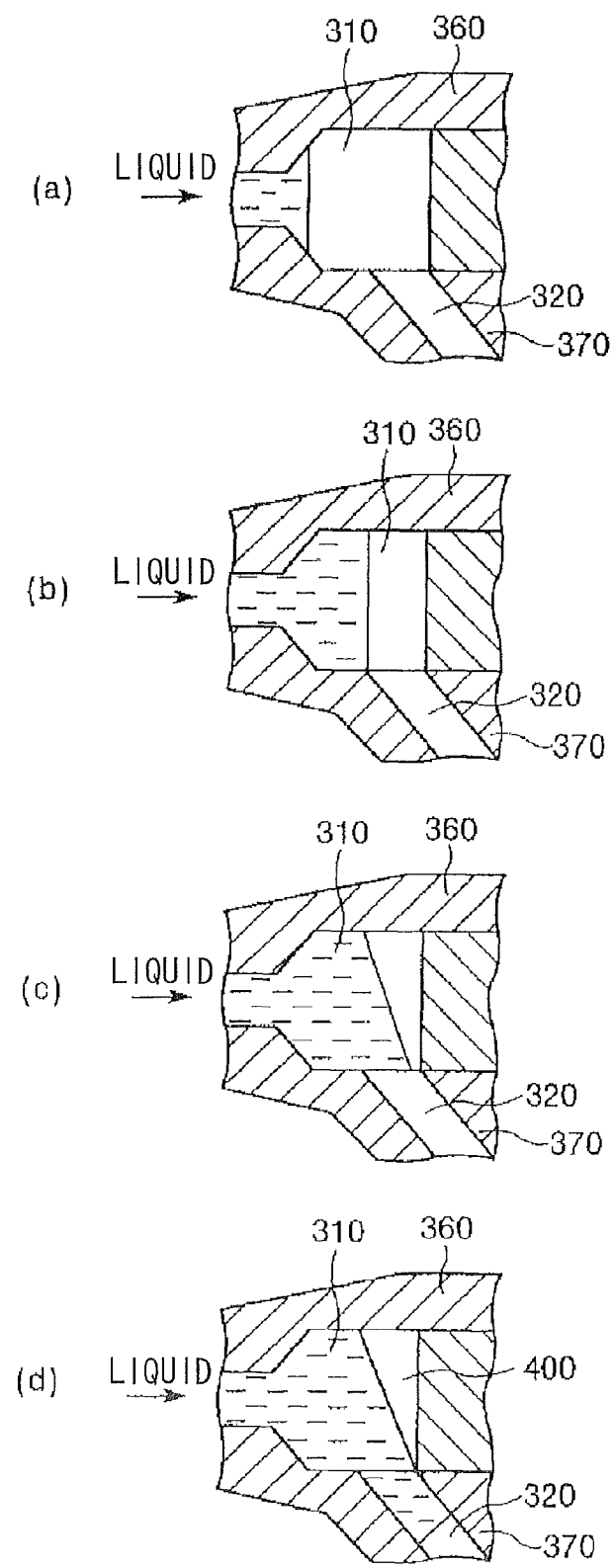
FIG. 20 are views illustrating operations of a conventional indwelling needle assembly.
Figure 21:
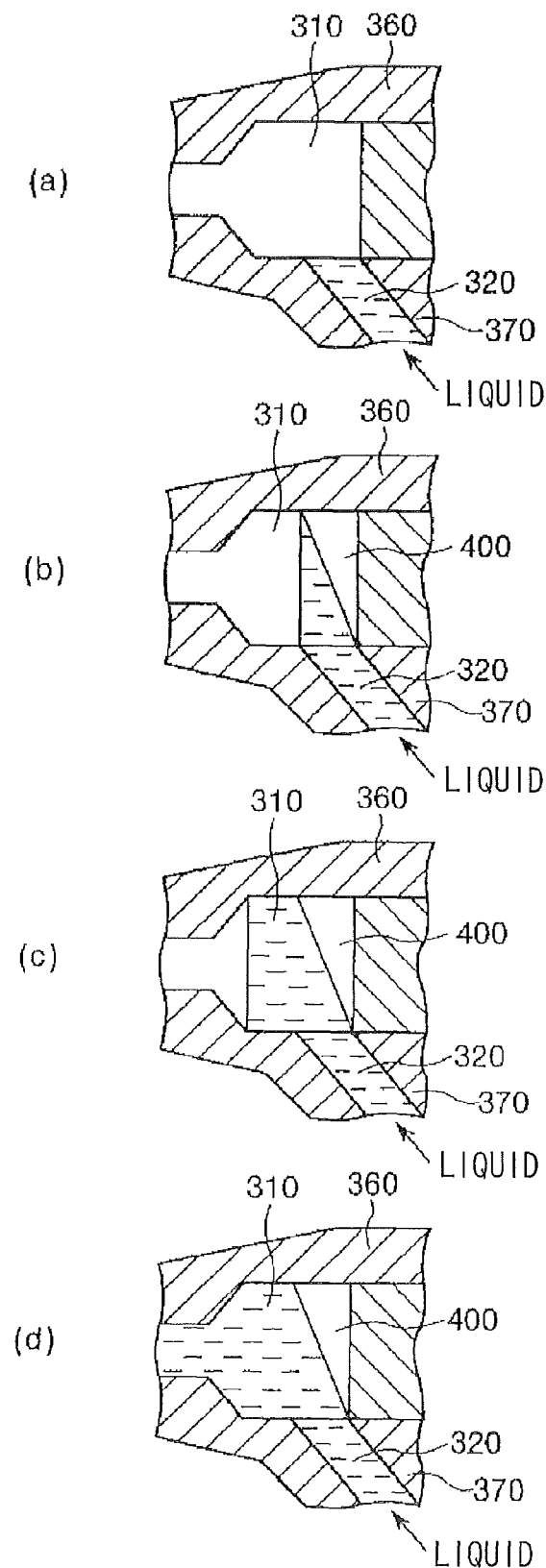
FIG. 21 are views illustrating operations of the conventional indwelling needle assembly.

FIGS. 20 and 21 are views illustrating operations of a conventional indwelling needle assembly, in which the outer needle hub thereof is not provided with a step section. In FIGS. 20 and 21, the right side is "proximal" and the left side is "distal," respectively.

First, in the conventional indwelling needle assembly, in the case that liquid flows in a flow path 310 of a main pipe 360 from the distal side toward the proximal side, and then flows into a branch flow path 320 of a side pipe 370, as shown in parts (a) to (d) of FIG. 20, bubbles (air) 400 tend to remain in the portion of the flow path 310 of the main pipe 360 that is in the vicinity of the side pipe 370.

In addition, in the conventional indwelling needle assembly, in the case that liquid flows into the branch flow path 320 of the side pipe 370 from the proximal side toward the distal side, and then flows into the flow path 310 of the main pipe 360, as shown in parts (a) to (d) of FIG. 21, similar to the above-mentioned case, bubbles 400 also are left in the portion of the flow path 310 of the main pipe 360 that is in the vicinity of the side pipe 370.

Figure 13:
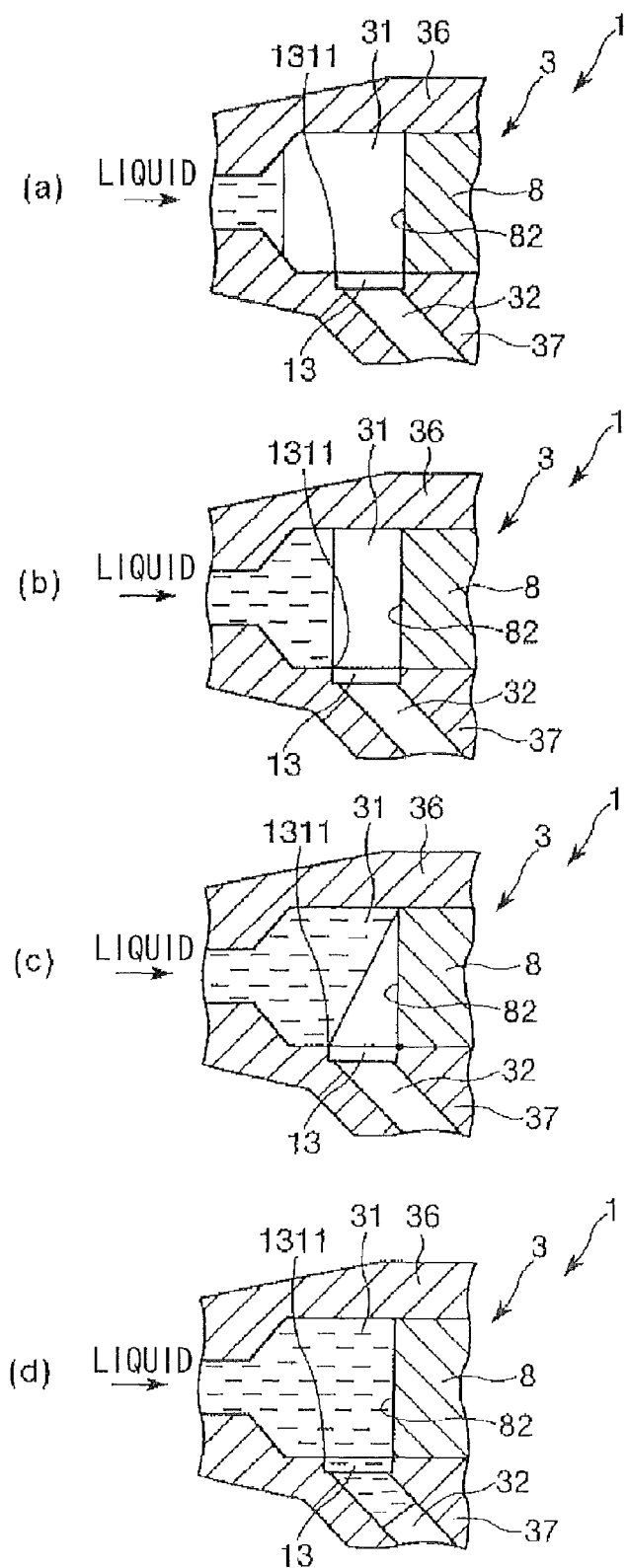
FIG. 13 is a view illustrating operations of the indwelling needle assembly shown in FIG. 1.

In contrast thereto, in the indwelling needle assembly 1 according to the present embodiment, in the case that liquid flows in the flow path 31 of the main pipe 36 from the distal side toward the proximal side, and then flows into the branch flow path 32 of the side pipe 37, as shown in part (a) of FIG. 13, a portion of the liquid, which flows along the part of the inner surface of the main pipe 36 that is located on the side on which the branch flow path 32 is located, is temporarily (momentarily) stopped (i.e., is reduced in speed in the axial direction of the flow path 31) at the edge 1331 of the step section 13 due to surface tension, as shown in parts (b) and (c) of FIG. 13.

On the other hand, portions of the liquid, which flow along other parts of the inner surface of the main pipe 36, flow without being reduced in speed in the axial direction of the flow path 31. Therefore, while a portion of the liquid, which flows along the part of the inner surface of the main pipe 36 that is located on a side on which the branch flow path 32 is located, is stopped, portions of the liquid apart therefrom, which flow along the other parts of the inner surface, flow along the distal end surface 82 of the seal member 8, from the upper side toward the lower side thereof, as shown in FIG. 13. Consequently, as shown in part (d) of FIG. 13, bubbles are sent out into the branch flow path 32, and such bubbles are discharged to the exterior via the branch flow path 32. In other words, after a condition is attained, in which the space in the flow path 31 of the main pipe 36 that is in the vicinity of the side pipe 37 is filled with liquid, the remaining liquid flows from the flow path 31 into the branch flow path 32. In this manner, it is possible to prevent a problem in which bubbles remain in the portion of the flow path 31 of the main pipe 36 that is in the vicinity of the side pipe 37.

Figure 14:
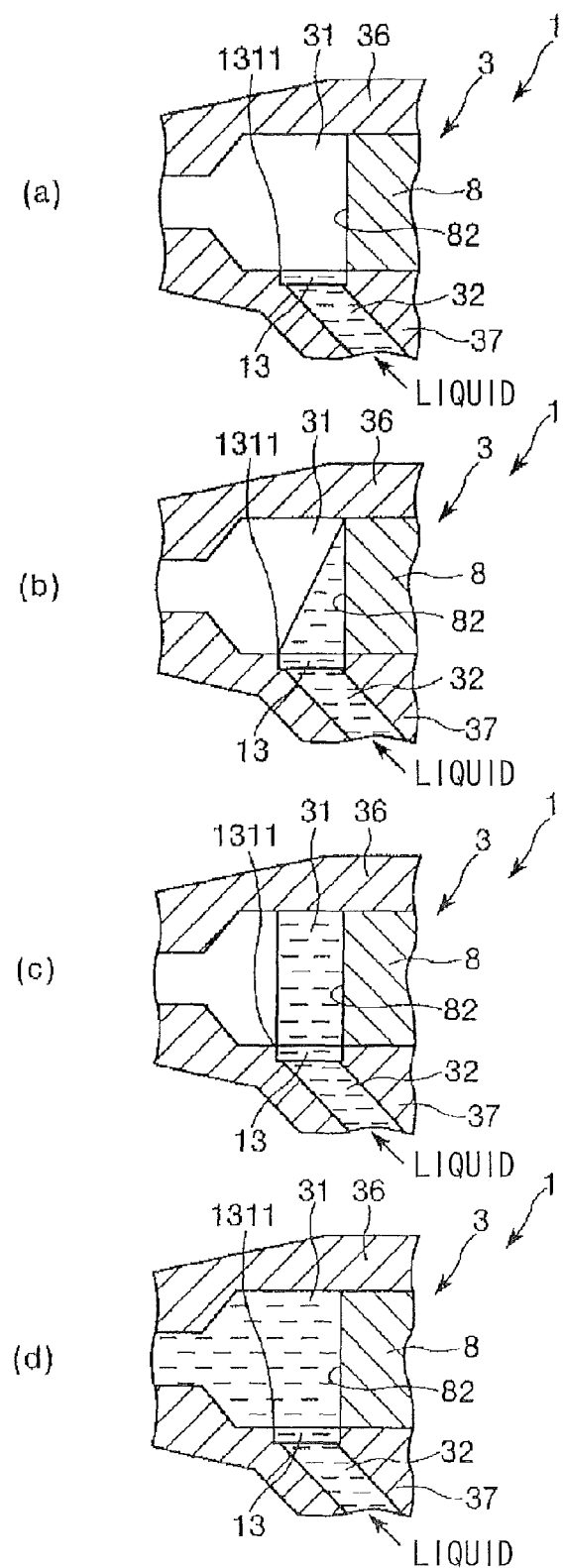
FIG. 14 is a view illustrating operations of the indwelling needle assembly shown in FIG. 1.

Further, in the indwelling needle assembly 1 of the present embodiment, in the case that liquid flows in the branch flow path 32 of the side pipe 37 from a proximal side toward a distal side thereof, and further flows into the flow path 31 of the main pipe 36, as shown in (a) to (d) of FIG. 14, a portion of the liquid is momentarily stopped at the edge 1331 of the step section 13 due to surface tension, while other portions of the liquid flow along the distal end surface 82 of the seal member 8, from the lower side toward the upper side in FIG. 14. Consequently, bubbles are sent out into the flow path 31, and such bubbles are discharged to the exterior via the flow path 31. In this manner, it is possible to prevent a problem in which bubbles remain in the portion of the flow path 31 of the main pipe 36 that is in the vicinity of the side pipe 37.

Next, an example of a method of using the indwelling needle assembly 1 (in a case of puncturing a blood vessel) (i.e., operations thereof) will be described in detail below.

[1] The indwelling needle assembly 1, which is placed in an assembled state (see FIGS. 1, 3 and 7), and a connector, which is attached to an end portion of an infusion line, is connected preliminarily to the connector 72, so that an infusion liquid from the infusion line can be supplied.

Incidentally, in this case, a predetermined portion of the tube 7 or the infusion line is preliminarily pinched, for example, by a clamp (an example of a flow path opening/closing means), so as to close the lumen of the tube 7 or the infusion line.

[2] Next, closure of the tube 7 or the infusion line with the clamp or the like is released, whereupon the infusion liquid from the infusion line starts to be introduced through the tube 7 into the outer needle hub 3.

The infusion liquid, which is introduced into the outer needle hub 3, fills the branch flow path 32 and the flow path 31 on the distal side relative to the seal member 8, and the infusion liquid is introduced into the lumen 21 of the outer needle 2, whereby the lumen 21 of the outer needle 2 is primed with the infusion liquid. In this instance, a part of the infusion liquid flows out via the tip opening 22 of the outer needle 2. As mentioned above, during the priming operation, the step section 13 makes it possible to securely remove air, which may be present in the flow path 31 and the branch flow path 32 in the outer needle hub 3, and to prevent bubbles from remaining in the flow path 31.

[3] After completion of priming in this manner, the tube 7 or the infusion line is again set in a closed state with a clamp or the like. Then, the wings 12a and 12b are closed by pinching them with the fingers, and using the wings 12a and 12b as a gripping part (operating part), the outer needle 2 and the inner needle 4, which are arranged together in an integral fashion, are made to puncture a blood vessel (vein or artery) of a patient.

When the puncturing operation is conducted on the blood vessel by gripping the wings 12a and 12b in this manner, the puncturing angle is made smaller, that is, the outer needle 2 and the inner needle 4 are arranged more closely in parallel in relation to the blood vessel, compared to a case in which the puncturing operation is carried out by directly gripping the outer needle hub 3. Consequently, the puncturing operation is easy to carry out, and the burden on the patient's blood vessel is alleviated.

When the outer needle 2 has captured (has securely reached the inside of) the blood vessel, the internal pressure (blood pressure) in the blood vessel causes blood to flow back in the proximal direction through the groove 44 of the inner needle 4, and then through the lumen 21 of the outer needle 2, so that flow of blood can be confirmed in at least one of the outer needle 2, the outer needle hub 3, the inner needle hub 5 and the tube 7, for which inside visibility has been provided.

After confirmation of blood flow, the outer needle 2 is advanced along the inner needle 4, using the inner needle 4 as a guide, by a very short distance in the distal direction.

In this case, the finger holder part 6 is pressed in the distal direction while the finger holder part 6 is lifted (in the manner of being lifted) in the projecting direction thereof (upward direction in FIG. 3), whereby the outer needle 2 is moved in the distal direction. This ensures that the outer needle 2 can be moved in a straight line along the center axis $O_1$, that is, along the direction of the center axis $O_1$, without the outer needle 2 becoming bent. Consequently, the outer needle 2 can be advanced smoothly.

In addition, during puncturing of the blood vessel in this manner, since the lumen 21 of the outer needle 2 already has been primed with the infusion liquid, erroneous penetration of a bubble or bubbles into the blood vessel is securely prevented, and safety is extremely high.

Further, the tube 7 is connected to a proximal portion of the outer needle hub 3, and in the assembled state, the center axis $O_1$ of the outer needle 2 and the center axis $O_2$ at the distal portion of the tube 7 are substantially parallel to each other. Therefore, the tube 7 does not obstruct puncturing operations by the outer needle 2 and the inner needle 4, and excellent operability is ensured.

[4] When the blood vessel has been captured by the outer needle 2 (i.e., when the outer needle 2 has been moved to a target position), the outer needle 2 or the outer needle hub 3 is fixed by one hand, while the inner needle hub 5 is gripped by the other hand and pulled in the proximal direction. Consequently, operations (motions) ranging from a motion of pulling the inner needle 4 out of the outer needle 2 to release of the protector 9 from the outer needle hub 3 are carried out sequentially and continuously. More specifically, first, the inner needle 4 is moved in the proximal direction, and then the inner needle 4 is pulled out from the outer needle 2.

[5] When the inner needle 4 has further been moved in the proximal direction and the needle tip 41 has passed through the slit 81, the seal member 8, which has a self-closing property, closes the slit 81 under its own elastic force. This ensures that leakage of liquid through the slit 81 can be prevented from occurring, whereby an aseptic condition inside the outer needle hub 3 and the infusion line is assured.

[6] When the inner needle 4 is moved further in the proximal direction, and until the needle tip 41 reaches the proximal side of the shutter member 94, as shown in FIG. 8, the shutter member 94 is opened under its own elastic force, resulting in the second posture that closes off the inner needle passage 931. When the shutter member 94 has thus been placed in the second posture, even if the needle tip 41 of the inner needle 4 tends to move so as to return again in the distal direction, the needle tip 41 abuts against the shutter member 94 and therefore cannot return to its former position.

[7] When the inner needle 4 is moved further in the proximal direction, and until the inner needle 4 reaches the proximal side of the lock member 933, as shown in FIG. 9, rotation of the lock member 933 is permitted, and the inner member 93 of the protector 9 moves in the proximal direction relative to the protector cover 92.

On the other hand, when the inner needle hub 5 is pulled in the proximal direction, the inner member 93 is moved as a result of being pulled through the connection member 20 in the proximal direction. When the distal portion of the inner member 93 reaches the proximal side of the projections 923 of the protector cover 92, as shown in FIG. 10, the projections 923 move toward the center axis of the inner needle 4. This permits the protector 9 to be moved in the proximal direction relative to the outer needle hub 3.

[8] When the inner member 93 is moved in the proximal direction, and until the projections 932 of the inner member 93 abut against the proximal-side edge portions 926 of the slots 925 in the protector cover 92, as shown in FIG. 10, the inner member 93 and the protector cover 92 are moved in unison in the proximal direction, whereby the protector 9 becomes separated (released) from the outer needle hub 3.

[9] In addition, due to the restoring force of the connection member 20, the inner member 93 is pulled in the proximal direction and is moved in the proximal direction relative to the inner needle 4. Also, as shown in FIG. 11, the needle tip 41 presses a bottom portion 935 of the lock member 933. Consequently, the lock member 933 is oriented such that the tip portion 934 thereof is oriented away from the inner needle 4 (oriented upwardly in FIG. 11), Then, the inner needle 4 makes contact with the bottom portion 935 of the lock member 933, and such an orientation is maintained.

[10] Due to the restoring force of the connection member 20, the inner member 93 is moved further in the proximal direction relative to the inner needle 4. Also, as shown in FIG. 11, the needle tip 41 of the inner needle 4 abuts against the shutter member 94.

Further, in a condition where the needle tip 41 is in abutment against the shutter member 94, the inner member 93 is biased in the proximal direction by the restoring force of the connection member 20, whereby such a condition can be maintained.

In addition, the connection member 20 has a length such that, in a maximally expanded state, the needle tip 41 remains contained within the inner member 93. Therefore, the protector 9 can be prevented from slipping off from the needle tip 41. Accordingly, the condition in which the protector 9 covers the needle tip 41 can reliably be maintained.

[11] Next, the tube 7, which is inserted in the tube containing section 52 of the inner needle hub 5, is detached through the groove 521.

After the inner needle 4 has been pulled out from the outer needle 2 in this manner, the inner needle 4 and the inner needle hub 5 are rendered useless, and therefore the inner needle 4 and the inner needle hub 5 are discarded.

The needle tip 41 of the inner needle 4 is covered by the protector 9. More specifically, the needle tip 41 is prevented from moving toward the distal side and beyond the shutter member 94 so as to protrude from the distal end of the protector 9. Therefore, an accident, in which a person in charge of discarding the inner needle 4 or the like might stick his or her finger with the needle tip 41 by mistake, is prevented from occurring.

[12] Subsequently, the wings 12a and 12b are opened, and are fixed to the skin using a pressure sensitive adhesive tape or the like. In addition, closure of the tube 7 or the infusion line with the clamp or the like is released, whereby supply of the infusion liquid is started.

The infusion liquid supplied from the infusion line is injected into the patient's blood vessel while passing through the lumen or inner cavities of the connector 72, the tube 7, the outer needle hub 3, and the outer needle 2, respectively.

As has been described above, in accordance with the indwelling needle assembly 1, it is possible to prevent a problem in which bubbles (air) remain in a portion of the flow path 31 of the main pipe 36, which is in the vicinity of the side pipe 37, during times when liquid is allowed to flow therethrough.

Incidentally, the configuration of the step section 13 is not limited to that described above. Another configuration example of the step section 13 will be described below, referring primarily to differences from the step section 13 according to the aforementioned first embodiment. In the following explanation, descriptions of the same items common to the above embodiment will be omitted.

As shown in FIG. 15, in this configuration example, as shown in plan view, concerning the opening 131 in the step section 13, a rectilinear portion 1311 (edge 1331) constituting a distal end thereof, a rectilinear portion 1314 (edge 1334) constituting a proximal end of the opening 131, a rectilinear portion 1313 (edge 1333) constituting an upper-side end in FIG. 15, and a rectilinear portion 1312 (edge 1332) constituting a lower-side end in FIG. 15 coincide (are in contact) respectively with the distal end, the proximal end, the upper-side end in FIG. 15, and the lower-side end in FIG. 15 of the tip opening 321 of the branch flow path 32.

Incidentally, either one, two, or three of the rectilinear portions 1311 to 1314 of the opening 131 may be in contact with the tip opening 321.

In addition, as shown in FIG. 16, in this embodiment, in plan view, the opening 131 in the step section 13 does not include the tip opening 321 of the branch flow path 32. More specifically, a rectilinear portion 1314 (1334) of the opening 131 is located between the distal end and the proximal end of the tip opening 321 (in the configuration shown in the figure, in the vicinity of the tip opening 321).

Further, the shape of the opening 131 in the step section 13 is not limited to being a rectangle. For example, as shown in parts (a) to (h) of FIG. 17, the shape may be a polygon like a tetragon, such as a trapezoid, etc., a triangle, a pentagon, a hexagon, etc., a semicircle, a semi-ellipse, or any combination of such shapes.

Second Embodiment

Figure 18:
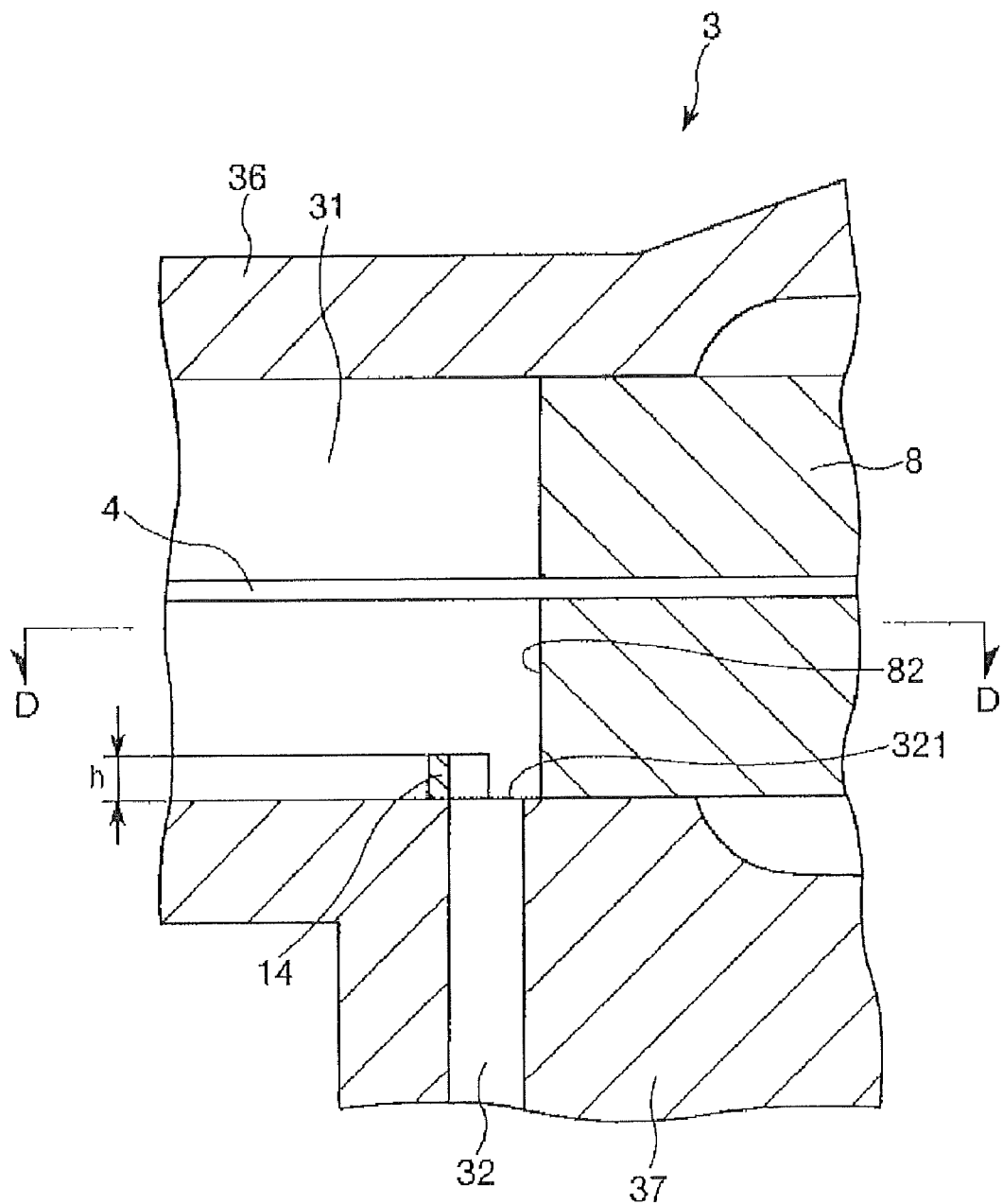
FIG. 18 is a sectional view showing a major part of an outer needle hub according to a second embodiment, in a case where the medical instrument according to the present invention is applied to an indwelling needle assembly.
Figure 19:
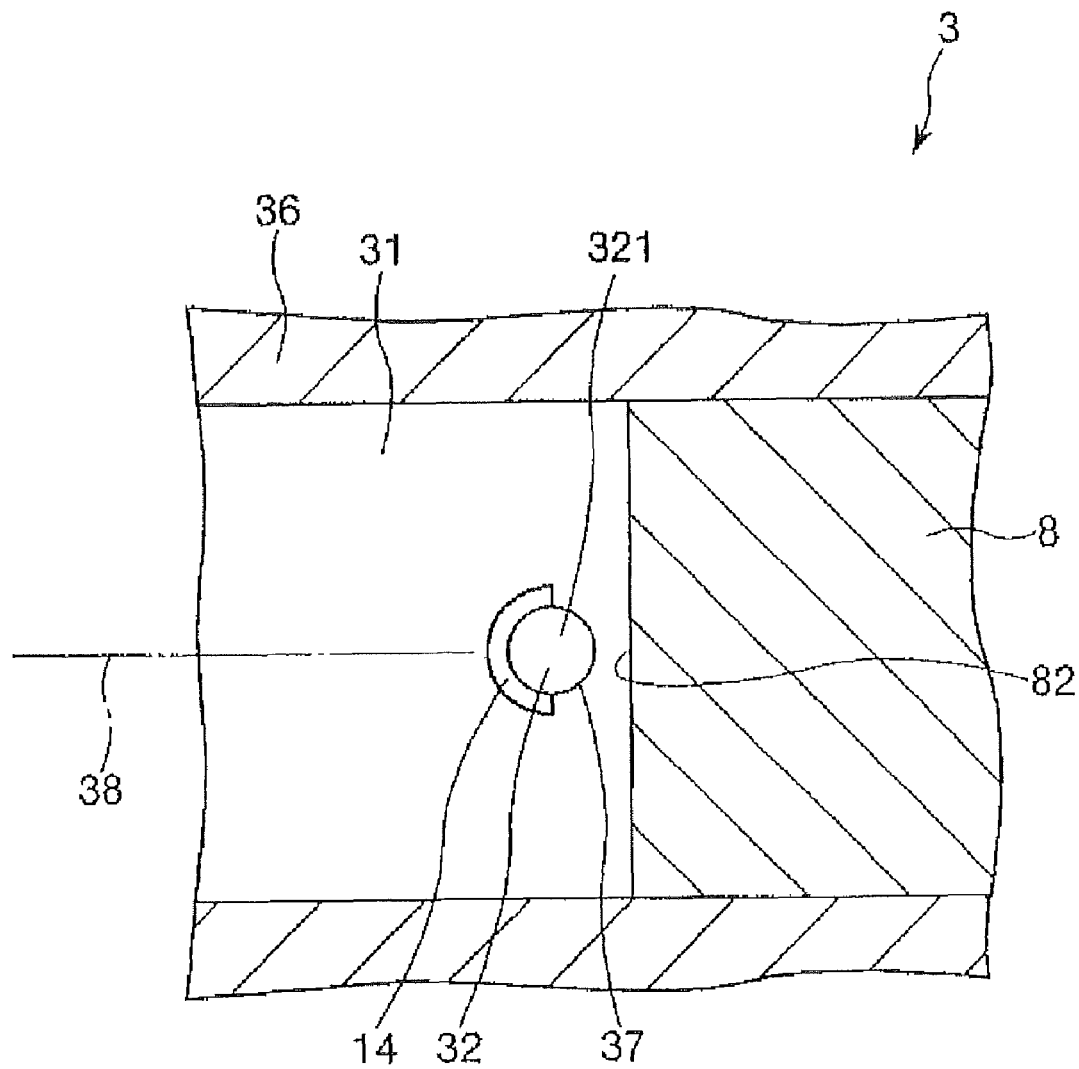
FIG. 19 is a sectional view taken along line D-D of FIG. 18.

FIG. 18 is a sectional view showing a major part of an outer needle hub according to a second embodiment, in a case where the medical instrument according to the present invention is applied to an indwelling needle assembly. FIG. 19 is a sectional view taken along line D-D of FIG. 18.

A second embodiment of the invention will be described below, referring primarily to differences from the first embodiment described above. In the following explanation, descriptions of the same items common to the above embodiment will be omitted.

As shown in FIGS. 18 and 19, in the indwelling needle assembly 1 according to the second embodiment, an outer needle hub 3 is provided with a wall part (projection) 14, which serves as a speed reducing means.

The wall part 14 is formed to project on an inner surface of a main pipe 36. The wall part 14 is located on a distal side (i.e., the upstream side with reference to the flow of liquid from a side of the main pipe 36 toward a side of the side pipe 37)

relative to a tip opening 321 of a branch flow path 32 of the side pipe 37, which is connected to the flow path 31 of the main pipe 36 and is located in the vicinity of the tip opening 321.

In addition, the wall part 14 is shaped so as to cover substantially the entire part of the tip opening 321, as viewed in the axial direction of the main pipe 36 (i.e., as the proximal side is viewed from the distal side). In the configuration shown in the figures, the wall part 14 is formed along a profile of the tip opening 321 and has a semicircular shape in plan view (see FIG. 19).

As a result of the wall part 14, liquid flowing toward the wall part 14 can temporarily (momentarily) be dammed up (i.e., it is possible to reduce the speed, in the axial direction of the flow path 31, of a portion of the liquid that flows along the part of the inner surface of the main pipe 36, which is located on a side on which the branch flow path 32 is located). Consequently, it is possible to prevent a problem in which bubbles (air) remain in the portion of the flow path 31 of the main pipe 36, which is located in the vicinity of the tip opening 321 of the side pipe 37.

Moreover, the height h of the wall part 14 is not particularly limited. The height h is set appropriately according to various conditions, such as the diameter of the flow path 31 (the inside diameter of the main pipe 36), the diameter of the branch flow path 32 (the inside diameter of the side pipe 37), etc. The diameter is preferably about 0.01 to 3 mm, and more preferably, about 0.02 to 1 mm. This ensures that the liquid can be dammed up (the speed of the liquid can be reduced) appropriately, whereby it is possible to more securely prevent the problem in which bubbles remain in the portion of the flow path 31 of the main pipe 36 that is located in the vicinity of the tip opening 321 of the side pipe 37.

According to the indwelling needle assembly 1 of the present embodiment, an effect equivalent to that of the indwelling needle assembly 1 according to the first embodiment described above can be obtained.

Figure 22:
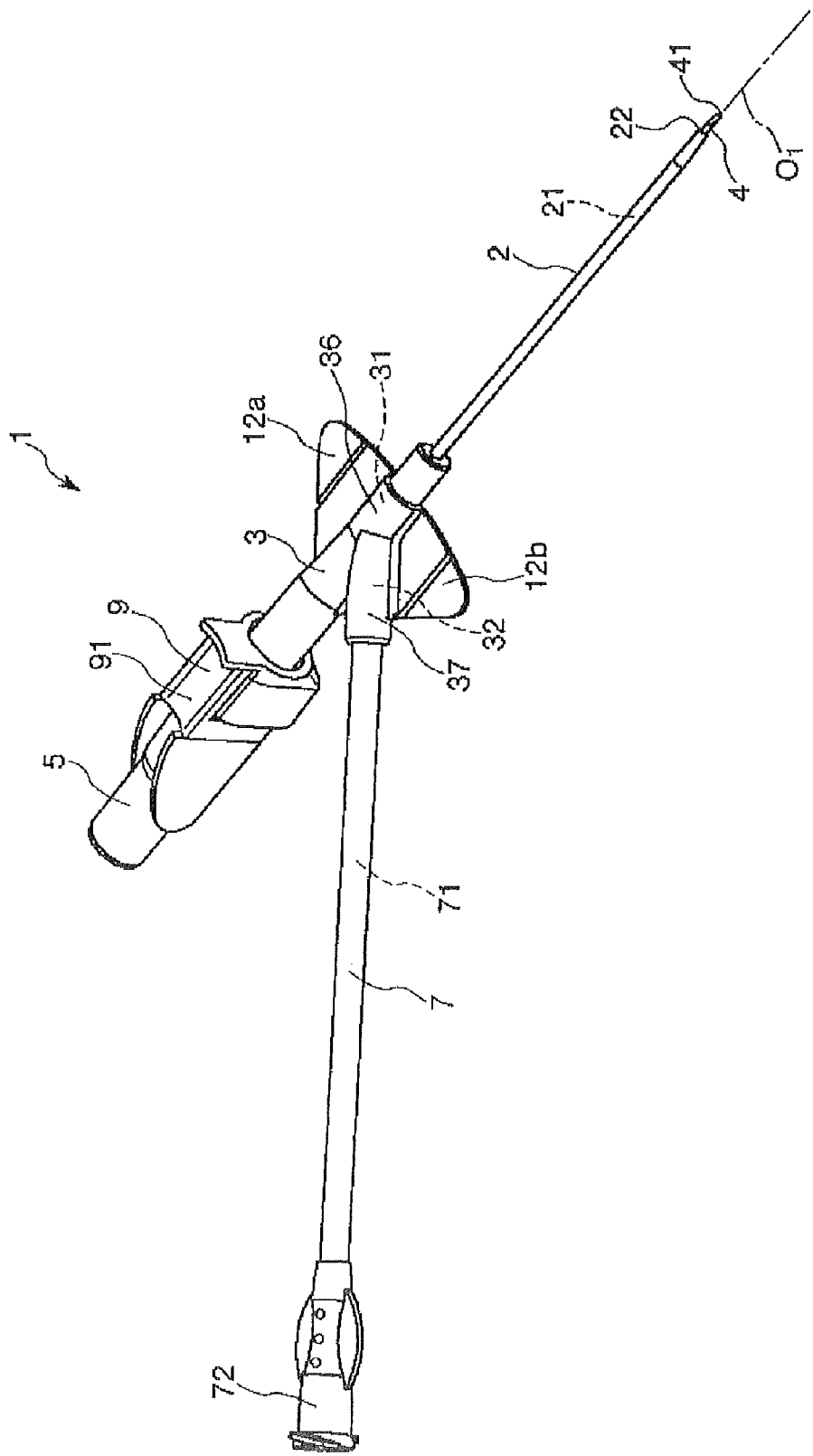
FIG. 22 is a perspective view showing a further configuration example, in a case where the medical instrument according to the present invention is applied to an indwelling needle assembly.

While, based on the embodiments shown in the drawings, a case has been described above in which the medical instrument according to the present invention is applied to an indwelling needle assembly, the invention is not limited to such embodiments, and parts constituting the indwelling needle assembly can be replaced by other parts of arbitrary configurations, which can exhibit functions equivalent thereto. For instance, except for the characteristic features thereof, the indwelling needle assembly (medical instrument) of the present invention may be of the same shape as described in U.S. Pat. No. 6,749,588, which was mentioned in the background art above as Patent Document 1. Examples of the indwelling needle assembly include the one shown in FIG. 22. Further, in the present invention, other arbitrary components or structures may be added thereto.

In addition, the present invention may be constituted by a combination of two or more structures (features) arbitrarily chosen from the embodiments described above.

In addition, the present invention is not limited to use as an indwelling needle assembly in a state of being inserted in a blood vessel. For example, the invention also is applicable to indwelling needle assemblies, which are capable of being inserted into an abdominal cavity, a thoracic cavity, a lymph vessel, a vertebral canal, or the like.

Also, in the present invention, the shape of the slit in the seal member (sealing means) is not limited to being a straight line segment. For example, other shapes including the shape of a cross, capital Y, capital T, capital H, etc., may also be adopted.

In addition, the medical instrument according to the present invention is not limited to being used as an indwelling needle assembly. For example, the medical instrument may be a predetermined instrument (member) of an indwelling needle assembly, and more specifically, an instrument composed of an outer needle and an outer needle hub fixed to a proximal portion of the outer needle. Other examples of medical instruments include a branched connector (a bifurcated branched connector) such as a Y-pipe, a T-pipe, etc. Incidentally, in the case of a Y-pipe, any of the flow paths may be set as a branch flow path of a side pipe.

Moreover, in the case of applying the present invention to a branched connector, examples of usable sealing means (sealing members) include a forceps (clamp member) capable of damming up (sealing) and opening the flow path of the main pipe, and a breakable clip chip, which opens the flow path of the main pipe when it is broken.

INDUSTRIAL APPLICABILITY

The medical instrument according to the present invention includes a main pipe and a side pipe having a branch flow path branching from a flow path of the main pipe, wherein a speed reducing means is provided for reducing a speed, in an axial direction of the main pipe, of a portion of a liquid that flows in the flow path of the main pipe, the portion being a portion that flows along a part of an inner surface of the main pipe, which is located on a side of the main pipe on which the branch flow path is located. Therefore, it is possible to prevent a problem in which bubbles remain in the portion of the flow path of the main pipe, which is located in the vicinity of the side pipe. Accordingly, the medical instrument according to the present invention has industrial Applicability.

The invention claimed is:

1. A medical instrument comprising a main pipe and a side pipe having a branch flow path branching from a flow path of the main pipe,
   wherein speed reducing means is provided for reducing a speed, in an axial direction of the main pipe, of a portion of liquid that flows in the flow path of the main pipe, the portion being a portion that flows along a part of an inner surface of the main pipe, which is located on a side of the main pipe on which the branch flow path is located,
   the speed reducing means has an opening formed in the inner surface of the main pipe,
   the flow path of the main pipe and a tip opening of the branch flow path of the side pipe communicate with each other by way of the opening of the main pipe, and
   the opening of the main pipe is greater than the tip opening of the branch flow path.

2. The medical instrument according to claim 1,
   wherein the opening of the main pipe has a profile having a rectilinear portion substantially perpendicular to the axis of the main pipe, and
   the rectilinear portion is located on an upstream side with respect to a flow of liquid from a side of the main pipe toward a side of the side pipe.

3. The medical instrument according to claim 1, wherein the speed reducing means is a step section, which forms a space between the opening of the main pipe and a tip, on the main pipe side, of the branch flow path.

4. The medical instrument according to claim 1, wherein the step section has, at an edge thereof confronting the opening, an edge with an angle of not more than 90°.

5. The medical instrument according to claim 1, wherein sealing means for sealing the flow path of the main pipe is provided at a part of the flow path of the main pipe that is located on a downstream side, with respect to the flow of liquid from a side of the main pipe toward a side of the side pipe, relative to the branch flow path.

6. The medical instrument according to claim 1, comprising an indwelling needle provided on a tip side of the main pipe.

7. The medical instrument according to claim 6, wherein the indwelling needle comprises a hollow outer needle in which an inner needle is inserted, and an outer needle hub, which is fixed to a base end part of the outer needle, incorporates therein the main pipe, the side pipe and the speed reducing means.

8. A medical instrument comprising a main pipe and a side pipe having a branch flow path branching from a flow path of the main pipe,
    wherein speed reducing means is provided for reducing a speed, in an axial direction of the main pipe, of a portion of liquid that flows in the flow path of the main pipe, the portion being a portion that flows along a part of an inner surface of the main pipe, which is located on a side of the main pipe on which the branch flow path is located,
    the speed reducing means comprises a projection which is formed to project on the inner surface of the main pipe, and
    the projection is located on an upstream side, with respect to the flow of liquid from a side of the main pipe toward a side of the side pipe, relative to a tip opening of the branch flow path connected to the flow path of the main pipe, and which is located in the vicinity of the tip opening.

9. The medical instrument according to claim 8, wherein the projection has a shape which covers substantially an entire part of the tip opening of the branch flow path, as a proximal side of the main pipe is viewed from a distal side thereof in an axial direction.

10. The medical instrument according to claim 8, wherein the projection is formed along a profile of the tip opening of the branch flow path.

\* \* \* \* \*